US012594084B2

(12) United States Patent
Laser et al.

(10) Patent No.: US 12,594,084 B2
(45) Date of Patent: Apr. 7, 2026

(54) ULTRASOUND DEVICE FOR USE WITH SYNTHETIC CAVITATION NUCLEI

(71) Applicant: Applaud Medical, Inc., San Francisco, CA (US)

(72) Inventors: Daniel J. Laser, San Francisco, CA (US); William Behnke-Parks, San Francisco, CA (US); David Bell, San Francisco, CA (US); Matthew Hopcroft, San Francisco, CA (US); Kyle P. Morrison, Bothell, WA (US)

(73) Assignee: AVVIO Medical, Inc., San Francisco, CA (US)

( * ) Notice: Subject to any disclaimer, the term of this patent is extended or adjusted under 35 U.S.C. 154(b) by 1103 days.

(21) Appl. No.: 17/288,867

(22) PCT Filed: Oct. 25, 2019

(86) PCT No.: PCT/US2019/058227
§ 371 (c)(1),
(2) Date: Apr. 26, 2021

(87) PCT Pub. No.: WO2020/087049
PCT Pub. Date: Apr. 30, 2020

(65) Prior Publication Data
US 2022/0000509 A1        Jan. 6, 2022

Related U.S. Application Data

(60) Provisional application No. 62/751,370, filed on Oct. 26, 2018.

(51) Int. Cl.
*A61B 17/22*        (2006.01)
*A61B 17/225*        (2006.01)
(Continued)

(52) U.S. Cl.
CPC .. *A61B 17/22012* (2013.01); *A61B 17/22004* (2013.01); *A61B 17/2251* (2013.01);
(Continued)

(58) Field of Classification Search
CPC ...... A61B 18/0206; A61B 2017/22005; A61B 2017/22007; A61B 2017/22008;
(Continued)

(56) References Cited

U.S. PATENT DOCUMENTS 5,817,021 A * 10/1998 Reichenberger ... A61B 17/2202
601/3
6,007,499 A * 12/1999 Martin ................. A61B 8/4461
601/3
(Continued)

FOREIGN PATENT DOCUMENTS

EP            1591070 A1 * 11/2005 ....... A61B 17/22004
WO    WO-2018126080 A1 * 7/2018 ............. G16H 50/30

OTHER PUBLICATIONS

Frustrum. (2017). Merriam Webster Dictionary. http://merriam-webster.com/dictionary/frustum (Year: 2017).*
(Continued)

*Primary Examiner* — Keith M Raymond
*Assistant Examiner* — Johnathan Maynard
(74) *Attorney, Agent, or Firm* — Intrinsic Law Corp.

(57)        ABSTRACT

This invention relates generally to an ultrasound device configured to generate a frustum-shaped beam capable of fragmenting a plurality of biomineralizations located within a patient's body in combination with synthetic cavitation nuclei. The ultrasound device includes a transducer assembly comprising a plurality of ultrasound transducer elements, and a multi-channel amplifier circuit. Each channel of the multi-channel amplifier circuit is configured to actuate a distinct subset of the plurality of transducer elements. The
(Continued)

multi-channel amplifier circuit is configured to operate in each of a plurality of states, each state of comprising a set of frequencies at which each channel of the multi-channel amplifier circuit is configured to actuate the distinct subset of transducer elements. The multi-channel amplifier circuit is further configured to switch between the plurality of states, thereby causing the plurality of ultrasound transducer elements to produce a frustum-shaped beam.

36 Claims, 22 Drawing Sheets

(51) Int. Cl.
| | |
|---|---|
| *A61N 7/00* | (2006.01) |
| *B06B 1/02* | (2006.01) |
| *G10K 11/34* | (2006.01) |

(52) U.S. Cl.
CPC .............. *A61N 7/00* (2013.01); *B06B 1/0207* (2013.01); *A61B 2017/22008* (2013.01); *A61B 2017/22015* (2013.01); *A61B 2017/22028* (2013.01); *B06B 1/0292* (2013.01); *G10K 11/34* (2013.01)

(58) Field of Classification Search
CPC ........... A61B 2017/22009; A61B 2017/22014; A61B 2017/22015; A61B 2017/22025; A61B 2017/22027; A61B 2017/22028; A61B 2017/22088; A61B 17/22004; A61B 17/22012; A61B 2017/22017; A61B 2017/22018; A61B 17/2202; A61B 2017/22021; A61B 17/22022; A61B 2017/22024; A61B 17/22029
See application file for complete search history.

(56) References Cited

U.S. PATENT DOCUMENTS

| | | | | |
|---|---|---|---|---|
| 7,211,060 | B1 * | 5/2007 | Talish | G10K 11/004 |
| | | | | 600/407 |
| 2002/0145941 | A1 * | 10/2002 | Poland | G10K 11/346 |
| | | | | 367/11 |
| 2003/0028287 | A1 * | 2/2003 | Puskas | B06B 1/0269 |
| | | | | 700/266 |
| 2007/0055157 | A1 * | 3/2007 | Bohris | A61B 17/2255 |
| | | | | 601/4 |
| 2009/0012514 | A1 * | 1/2009 | Moonen | A61N 7/02 |
| | | | | 606/27 |
| 2011/0009734 | A1 * | 1/2011 | Foley | A61N 7/02 |
| | | | | 601/2 |
| 2011/0285244 | A1 * | 11/2011 | Lewis | B06B 1/023 |
| | | | | 310/317 |
| 2017/0245874 | A1 * | 8/2017 | Bailey | A61B 8/085 |
| 2017/0360413 | A1 * | 12/2017 | Rothberg | A61B 8/585 |
| 2018/0353777 | A1 * | 12/2018 | Dianis | A61B 8/14 |
| 2019/0290305 | A1 * | 9/2019 | Engles | A61N 7/00 |
| 2021/0275835 | A1 * | 9/2021 | Adam | A61N 7/00 |
| 2021/0346725 | A1 * | 11/2021 | Rousso | A61N 7/02 |
| 2022/0023670 | A1 * | 1/2022 | Emery | A61N 7/02 |

OTHER PUBLICATIONS

Frustum. (2018). Math is Fun. http://www.mathsisfun.com/definitions/frustum.html (Year: 2018).*

McAdams. Frustum. (2009). All Math Words Encyclopedia. Life is a Story Problem LLC. http://www.allmathwords.org/en/f/frustum.html. (Year: 2017).*

* cited by examiner

600

800

900

Carrier
920

Transducer Assembly
140

Belt
910

Frustum-Shaped Beam 150

Target Treatment Region 1110

Transducer Assembly 140

Single-Channel Amplifier Circuit 1120

Multi-Channel Amplifier Circuit 230

Ultrasound Device Belt
900

Transducer
Assembly
140

Posterior Face of Patient
1400

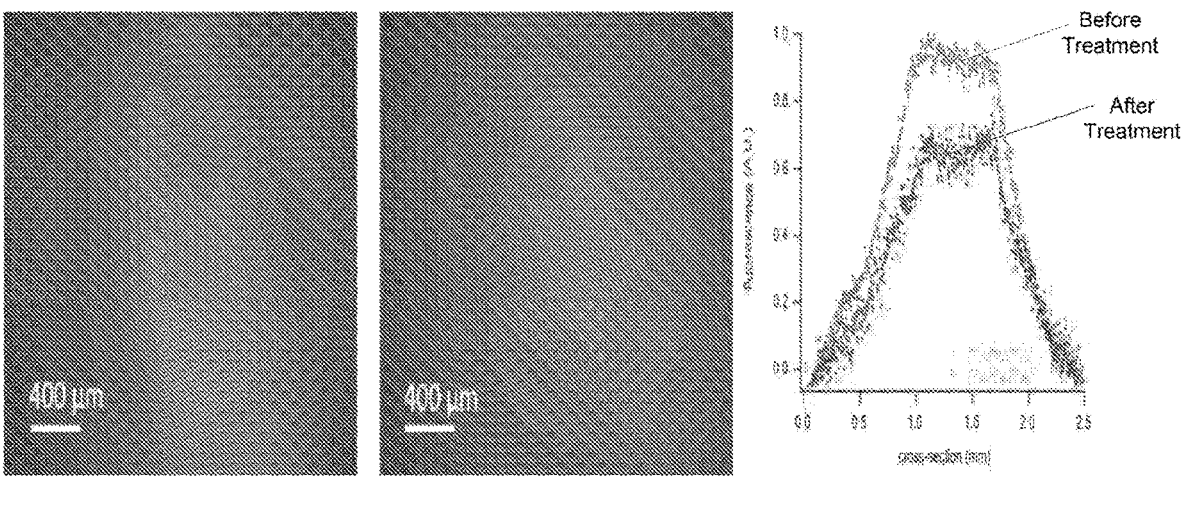
FIG. 18A          FIG. 18B          FIG. 18C

ULTRASOUND DEVICE FOR USE WITH SYNTHETIC CAVITATION NUCLEI

CROSS-REFERENCE TO RELATED APPLICATIONS

This application is a U.S. National Phase Application of International Application No. PCT/US2019/058227 filed Oct. 25, 2019, which claims the benefit of U.S. Provisional Application No. 62/751,370, filed Oct. 26, 2018, which is are hereby incorporated in its their entirety by reference.

TECHNICAL FIELD

These inventions are directed toward systems, devices, compositions, and methods for treating pathologies associated with biomineralizations. More particularly, these inventions are directed toward systems, devices, compositions, and methods for treating pathologies associated with biomineralizations by providing synthetic cavitation nuclei and a frustum-shaped beam from an ultrasound transducer to a portion of a patient's anatomy at which the biomineralizations are located.

BACKGROUND

A large number of pathologies are characterized in part by the presence of pathological biomineralizations. Examples include urinary stones, biliary stones, blood clots, fibroids, bone spurs, and atheromatous plaques.

Some medical interventions currently exist to treat these pathological biomineralizations. For example, pathological biomineralizations can be treated using extracorporeal shock wave lithotripsy treatment. In extracorporeal shock wave lithotripsy treatment, intense shockwaves are focused onto a biomineralization located, for example, in the urinary tract. The high intensity of these shockwaves can result in fragmentation of the biomineralization. However, these high intensity shockwaves can also result in injury to healthy tissue surrounding the biomineralization.

Therefore, therapeutic treatments for fragmentation of pathological biomineralizations that do not injure healthy tissue are desirable. However, existing minimally invasive therapies are not consistently efficacious or suffer from drawbacks such as lengthy treatment durations, or the need for expensive equipment, which can reduce access to the therapies. Embodiments of the disclosure herein address these and other shortcomings of the prior art.

SUMMARY

This invention relates generally to ultrasound devices that generate frustum-shaped beams that, when in combination with synthetic cavitation nuclei, are capable of treating at least one pathological biomineralization located within a patient's body.

In an aspect, the disclosure provides an ultrasound device that comprises a plurality of ultrasound transducer elements and a multi-channel amplifier circuit. The plurality of ultrasound transducer elements are arranged in an array and are contained within an external housing. The multi-channel amplifier circuit includes one or more channels. Each channel of the multi-channel amplifier circuit is configured to actuate a distinct subset of the plurality of ultrasound transducer elements. A subset of ultrasound transducer elements can include one or more ultrasound transducer elements. The multi-channel amplifier circuit is configured to operate in each of a plurality of states. Each state comprises a set of frequencies. Each set of frequencies comprises a frequency at which each channel of the multi-channel amplifier circuit is configured to actuate the distinct subset of the plurality of ultrasound transducer elements that is associated with the channel. Furthermore, the multi-channel amplifier circuit is configured to switch between the plurality of states. In other words, the multi-channel amplifier circuit is configured to perform frequency modulation. This frequency modulation causes the plurality of ultrasound transducer elements to produce a frustum-shaped beam.

A "frustum-shaped beam" comprises a plurality of longitudinal acoustic waves, each longitudinal acoustic wave of the plurality of longitudinal acoustic waves produced by one of the plurality of ultrasound transducer elements, and the constructive and destructive interference of the longitudinal acoustic waves yielding approximately uniform peak pressures throughout a frustum-shaped volume, when the beam is located within water or another medium having a comparable, uniform density. As referred to herein, a "peak pressure" refers to a minimum or maximum value of pressure of the longitudinal acoustic waves within the volume of the frustum-shaped beam. As referred to herein, "approximately uniform peak pressures" with regard to a frustum-shaped beam, refers to peak pressures of the longitudinal acoustic waves within the volume of the frustum-shaped beam being within 50% of a global maximum peak pressure of the longitudinal acoustic waves within the volume of the frustum-shaped beam.

In certain embodiments, the frequency and amplitude of the longitudinal acoustic waves comprising the frustum-shaped beam can vary over time, such that peak pressures of the frustum-shaped beam are between 0.5 megapascals and 10 megapascals, when measured in water. In an embodiment, the frequencies of the plurality of states of the multi-channel amplifier circuit can include frequencies between 200 hertz and 2,000,000 hertz. In some embodiments, the frequencies of the plurality of states of the multi-channel amplifier circuit can have a center frequency of about 500,000 hertz.

As mentioned above, the frustum-shaped beam can encompass a frustum-shaped volume. In some embodiments, the frustum-shaped beam can comprise a first frustum base, a second frustum base, and a first distance between the first frustum base and the second frustum base. The first frustum base is located a second distance from a surface of the ultrasound transducer assembly from which the plurality of ultrasound transducer elements produce the frustum-shaped beam. The first frustum base and the second frustum base are parallel to the surface of the ultrasound transducer assembly. In certain embodiments, an area of the first frustum base can be larger than an area of the second frustum base. In some embodiments, the first distance between the first frustum base and the second frustum base can be at least 12 centimeters. In certain embodiments, the second distance between the first frustum base and the surface of the ultrasound transducer assembly can be about 2 centimeters.

In some embodiments, the plurality of ultrasound transducer elements included in the ultrasound transducer assembly can be piezoelectric transducers. In alternative embodiments, the plurality of ultrasound transducer elements included in the ultrasound transducer assembly can be capacitive micromachined elements. In further embodiments, one or more of the plurality of ultrasound transducer elements included in the ultrasound transducer assembly can be apodized. In certain embodiments, the plurality of ultrasound transducer elements include at least 4 and at most 8 ultrasound transducer elements. In further embodiments, the plurality of transducer elements can include 4 ultrasound transducer elements.

In certain embodiments, the array in which the plurality of ultrasound transducer elements are arranged is a linear array. In alternative embodiments, the array in which the plurality of ultrasound transducer elements are arranged is a two dimensional array. In such embodiments, the two dimensional array has a first array distance and direction, a second array distance and direction, and an angle between the first and second array directions. In some embodiments, the first array distance can be between 50 millimeters and 150 millimeters, the second array distance can be between 20 millimeters and 60 millimeters, and/or the angle between the first and second array directions can be between 45 and 120 degrees. In a preferred embodiment, the first array distance is 100 millimeters, the second array distance is 30 millimeters, and the angle between the first and second array directions is 90 degrees.

In some embodiments, a space between each ultrasound transducer element of the plurality of ultrasound transducer elements and the nearest neighbor can be an air kerf of between 50 and 500 micrometers. In one preferred embodiment, the space between each ultrasound transducer element of the plurality of ultrasound transducer elements and the nearest neighbor is an air kerf of about 100 micrometers. In another preferred embodiment, the space between each ultrasound transducer element of the plurality of ultrasound transducer elements and the nearest neighbor is an air kerf of about 400 micrometers.

In certain embodiments, each channel of the multi-channel amplifier circuit can be associated with two transistors. In such embodiments, the two transistors associated with each channel can be configured to control the frequency at which the channel actuates the distinct subset of the plurality of ultrasound transducer elements associated with the channel, based on the state of the multi-channel amplifier circuit. Specifically, in some embodiments, the two transistors associated with each channel can be configured to operate in an alternating manner to cause the distinct subset of the plurality of ultrasound transducer elements associated with the channel to produce an acoustic wave at a frequency between 100 kHz and 10,000 kHz, based on the state of the multi-channel amplifier circuit. In such embodiments in which each channel of the multi-channel amplifier circuit is associated with two transistors, each channel of the multi-channel amplifier circuit can be further associated with an electrical filter that is configured to filter out high-frequency components from the acoustic wave produced by the distinct subset of the plurality of ultrasound transducer elements associated with the channel, in coordination with the two transistors.

In some further embodiments in which each channel of the multi-channel amplifier circuit is associated with two transistors, the multi-channel amplifier circuit can further include at least one power source that is configured to supply a constant voltage throughout a duration of a state of the multi-channel amplifier circuit. In some further embodiments, the at least one power source can further include at least two power sources, and each of the at least two power sources can be configured to supply a distinct constant voltage throughout a duration of a state of the multi-channel amplifier circuit. In such embodiments in which the multi-channel amplifier circuit includes at least two power sources, the multi-channel amplifier circuit can further include at least one multiplexer that is configured to connect the at least two power sources to the two transistors associated with each channel. Specifically, at a given point in time, the multiplexer can connect one or more of the at least two the power sources to the two transistors associated with each channel. In some embodiments, at a given point in time, there is a 1:1 connection between the power sources and the channels. In alternative embodiments, more than one power source can be connected to the two transistors associated with each channel. Furthermore, the multiplexer is capable of switching connections between the power sources and the two transistors associated with each channel. Therefore, at different points in time, the power sources can be differentially connected to the transistors associated with each channel.

In embodiments in which the multi-channel amplifier circuit includes the at least two power sources, each of the at least two power sources can further comprise a capacitor that is configured to charge at a charging rate such that the capacitor reaches a desired voltage during a period of time that is less than a duration of an off-state of the multi-channel amplifier circuit, where the off-state of the multi-channel amplifier circuit is defined by each channel of the multi-channel amplifier circuit actuating the associated subsets of ultrasound transducer elements at a frequency of 0 hertz.

In some embodiments, a quantity of power sources can be 7. In certain further embodiments, the multi-channel amplifier circuit can further comprise a central processing unit that is configured to control the switching between the plurality of states of the multi-channel amplifier circuit.

In certain embodiments, the ultrasound device disclosed herein is configured to insonate up to 10 cm of a length of a ureter of a patient at one time. In further embodiments, the ultrasound device disclosed herein is configured to insonate a ureter of a patient with a body-mass index less than or equal to 40. In some embodiments, a temperature of the ultrasound transducer assembly does not surpass 43 degrees Celsius during production of the frustum-shaped beam.

In certain embodiments, the ultrasound transducer assembly can further comprise a standoff pad that is attached to a surface of the transducer assembly from which the frustum-shaped beam is produced by the plurality of ultrasound transducer elements. In such embodiments, the standoff pad is configured to be placed in contact with skin of a patient at a location determined by using guidance from a pre-operative diagnostic tool. In even further embodiments, the standoff pad can be configured to be in uniform contact with skin of a patient's body with or without use of real-time imaging.

In some embodiments, the ultrasound device disclosed herein can further include a belt comprising a receptacle for the ultrasound transducer assembly. In such embodiments, the belt can be configured to secure the ultrasound transducer assembly to be placed in uniform contact with the skin of the patient's body. In further embodiments, the belt can be configured to secure the ultrasound transducer assembly at an angle relative to a plane of the skin of the patient's body.

In some embodiments, entry of the plurality of ultrasound transducer elements' operating variables as inputs into a computer-simulation program can generate a simulated beam having a spatially uniform peak pressure distribution within a volume, and a local minimum pressure within the volume that is within about 50% of a local maximum pressure within the volume. In some further embodiments, the simulated beam can have a local pressure within the volume of between 6 megapascals and 0.1 megapascals.

In another aspect, the disclosure provides a method for fragmenting at least one biomineralization located within a portion of a patient's body. The method includes locating an ultrasound transducer assembly at a treatment site and energizing the ultrasound transducer assembly to insonate the portion of the patient's body. The portion of the patient's body contains synthetic cavitation nuclei, and the insonation is effective to fragment the at least one biomineralization.

In some embodiments, the method can further include a step of locating the synthetic cavitation nuclei within the portion of the patient's body. In such embodiments, locating the synthetic cavitation nuclei within the portion of the patient's body can include administering a solution comprising the synthetic cavitation nuclei to the portion of the patient's body via a catheter with a first end located outside of the patient's body and a second end located inside or near the portion of the patient's body.

In certain embodiments, the synthetic cavitation nuclei can include a targeting moiety that has an affinity to the at least one biomineralization, thereby causing the synthetic cavitation nuclei to accumulate at a surface of the at least one biomineralization. In such embodiments, the targeting moiety can form a covalent bond with a chemical constituent of the at least one biomineralization.

In some embodiments, the ultrasound device can use a multi-channel circuit to actuate the ultrasound transducer assembly.

In some embodiments, the treatment site can be determined using guidance from at least one of a pre-operative diagnostic tool and a bony landmark of the patient. In additional embodiments, the treatment site can be determined without use of real-time imaging.

In some embodiments, the portion of the patient's body can be an upper half of a ureter, and locating the ultrasound transducer assembly at the treatment site can include placing the ultrasound transducer assembly in contact with a buffer material that is in contact with skin located on a posterior face of the patient's body. In alternative embodiments, the portion of the patient's body can be a lower half of a ureter, and locating the ultrasound transducer assembly at the treatment site can include placing the ultrasound transducer assembly in contact with a buffer material that is in contact with skin located on an anterior face of the patient's body.

In another aspect, the disclosure provides an ultrasound device that is configured to produce a frustum-shaped beam that has a first frustum base, a second frustum base, and a distance between the first frustum base and the second frustum base of at least 12 cm.

As discussed above, a "frustum-shaped beam" comprises a plurality of longitudinal acoustic waves, each longitudinal acoustic wave of the plurality of longitudinal acoustic waves produced by one of the plurality of ultrasound transducer elements, and the constructive and destructive interference of the longitudinal acoustic waves yielding approximately uniform peak pressures throughout a frustum-shaped volume, when the beam is located within water or another medium having a comparable, uniform density. In certain embodiments, the frequencies of the plurality of states of the multi-channel amplifier circuit can include frequencies between 200 hertz and 2,000,000 hertz. In some embodiments, the frequencies of the plurality of states of the multi-channel amplifier circuit can have a center frequency of about 500,000 hertz.

In some embodiments, the first frustum base can be a square area. In some further embodiments, the second frustum base can be a one-dimensional line. In certain embodiments, an area of the first frustum base can be larger than an area of the second frustum base.

In certain embodiments, the ultrasound device used to produce the frustum-shaped beam can include an ultrasound transducer assembly that further includes a plurality of ultrasound transducer elements contained within an external housing. The ultrasound transducer elements can be arranged to generate the frustum-shaped beam. In some embodiments, the plurality of ultrasound transducer elements can include at least 4 ultrasound transducer elements. In some embodiments, the plurality of ultrasound transducer elements can be piezoelectric transducers. In alternative embodiments, the plurality of ultrasound transducer elements can be capacitive micromachined transducers. In certain embodiments, one or more of the plurality of ultrasound transducer elements can be apodized.

In certain embodiments, the plurality of ultrasound transducer elements can be arranged in a linear array. In alternative embodiments, the plurality of ultrasound transducer elements can be arranged in a two dimensional array. In such embodiments, the two dimensional array has a first array distance and direction, a second array distance and direction, and an angle between the first and second array directions. In some embodiments, the first array distance can be between 50 millimeters and 150 millimeters, the second array distance can be between 20 millimeters and 60 millimeters, and/or the angle between the first and second array directions can be between 45 and 120 degrees. In a preferred embodiment, the first array distance is 100 millimeters, the second array distance is 30 millimeters, and the angle between the first and second array directions is 90 degrees.

In some embodiments, a space between each ultrasound transducer element of the plurality of ultrasound transducer elements and the nearest neighbor can be an air kerf of between 50 and 500 micrometers. In one preferred embodiment, the space between each ultrasound transducer element of the plurality of ultrasound transducer elements and the nearest neighbor is an air kerf of about 100 micrometers. In another preferred embodiment, the space between each ultrasound transducer element of the plurality of ultrasound transducer elements and the nearest neighbor is an air kerf of about 400 micrometers.

In some embodiments, the ultrasound device can further include a belt having a receptacle for the ultrasound transducer assembly. In such embodiments, the belt is configured to secure the ultrasound transducer assembly to a treatment site.

In certain embodiments, the frustum-shaped beam is capable of insonating up to 10 cm of a length of a ureter of a patient at one time. In further embodiments, the frustum-shaped beam is capable of insonating a ureter of a patient with a body-mass index less than or equal to 40. In some embodiments, a temperature of the ultrasound transducer assembly does not surpass 43 degrees Celsius during production of the frustum-shaped beam.

In some embodiments, entry of the plurality of ultrasound transducer elements' operating variables as inputs into a computer-simulation program can generate a simulated beam having a spatially uniform peak pressure distribution within a volume, and a local minimum pressure within the volume that is within about 50% of a local maximum pressure within the volume.

BRIEF DESCRIPTION OF THE DRAWINGS

The present application is further understood when read in conjunction with the appended drawings. For the purpose of illustrating the subject matter, there are shown in the drawings exemplary embodiments of the subject matter. However, the presently disclosed subject matter is not limited to the specific systems, devices, compositions, and methods disclosed. In addition, the drawings are not necessarily drawn to scale. In the drawings:

FIG. 18A is an image depicting a Calcein fluorescence-labeled aortic valve before treatment using synthetic cavitation nuclei and an ultrasound device according to the embodiments disclosed herein.

FIG. 18B is an image depicting a Calcein fluorescence-labeled aortic value after treatment using synthetic cavitation nuclei and an ultrasound device according to the embodiments disclosed herein.

FIG. 18C is a graph depicting an intensity transverse profile of the Calcein fluorescence-labeled aortic value before treatment and an intensity transverse profile of the Calcein fluorescence-labeled aortic value after treatment, normalized to the maximum intensity of the before sample, with background fluorescence subtracted.

DETAILED DESCRIPTION

Figure 1:
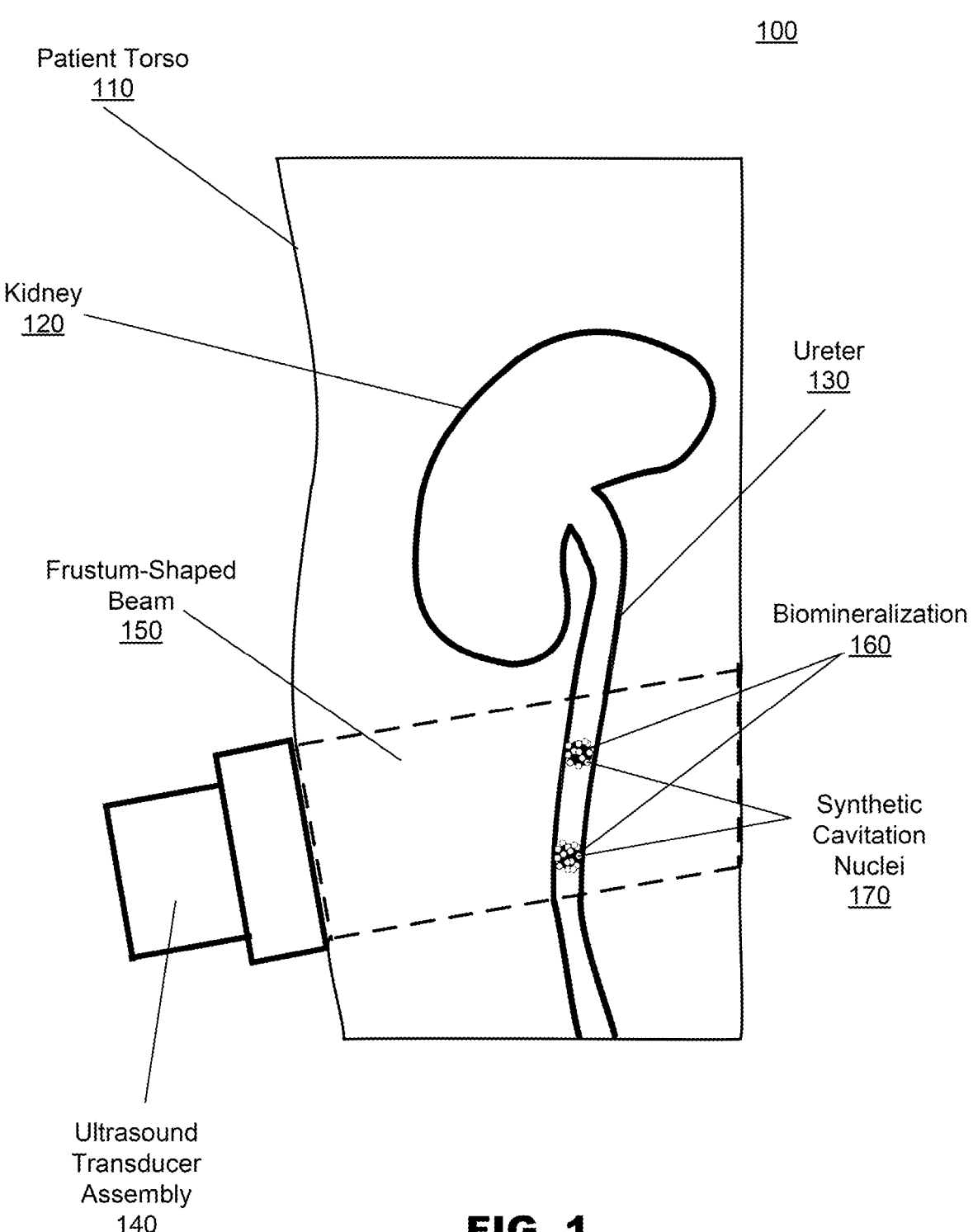
FIG. 1 provides a schematic illustration of an ultrasound device in accordance with an embodiment of the disclosed subject matter.

Systems, devices, compositions, and methods for treating one or more pathological biomineralizations within a portion of a patient's body are provided herein. The methods include locating a plurality of synthetic cavitation nuclei within the portion of the patient's body containing the biomineralizations, and insonating the portion of the patient's body with a frustum-shaped beam produced by an ultrasound device. In some embodiments, this insonation is capable of cavitating the synthetic cavitation nuclei, thereby causing fragmentation of the biomineralizations.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. In some embodiments, the term "about" encompasses +/−30% or +/−20% or +/−10% or +/−5% or +/− less than 5%.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a," "an," and "the" include plural referents unless the context clearly dictates otherwise. Thus, for example, a reference to "a material" is a reference to at least one of such materials and equivalents thereof known to those skilled in the art, and so forth.

Additionally, certain embodiments of the disclosed devices and/or associated methods can be represented by drawings which are included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

Any recited method can be carried out in the order of events recited or in any other order which is logically possible.

Systems

Systems, devices, compositions, and methods for treating one or more pathological biomineralizations located within a portion of a patient's body are included in the subject disclosure. Systems according to the subject embodiments include synthetic cavitation nuclei and an ultrasound device used in conjunction with one another to cause biomineralization fragmentation.

FIG. 1 provides a schematic illustration of a system in accordance with an embodiment of the disclosed subject matter. As is provided in FIG. 1, a system 100 includes biomineralizations 160 located within a vessel of a patient torso (or abdomen) 110. In the embodiment depicted in FIG. 1, the patient's vessel is a ureter 130. In alternative embodiments, the vessel may comprise any other anatomical vessel in the patient's body. For example, the vessel may comprise a blood vessel such as the aorta in alternative embodiments. In additional examples, biomineralizations can be located in a portion of a patient's body other than a vessel.

As shown in FIG. 1, a plurality of synthetic cavitation nuclei 170 have accumulated at a surface of each of the biomineralizations 160. An ultrasound transducer assembly 140 is located with respect to the patient's torso 110 such that the ultrasound transducer assembly 140 is capable of generating a frustum-shaped beam 150 within a volume of the patient's torso 110 that includes the plurality of synthetic cavitation nuclei 170 accumulated at the surfaces of the biomineralizations 160 within the patient's ureter 130. Note that the frustum-shaped beam 150 encompasses a volume such that multiple biomineralizations 160 spread throughout the patient's ureter 130 can be insonated simultaneously.

Biomineralizations can be bodily tissues in which minerals have become embedded. As a result, biomineralizations can be stiff or hard in texture. This change in material property of the affected tissue can result in a variety of disease pathologies. For example, this change in material property of the affected tissue can result in the tissue becoming stuck or lodged within a cavity of the patient's body, such as a vessel.

In the embodiment provided in FIG. 1, the biomineralizations 160 are urinary stones lodged in the ureter 130 within the patient's torso 110. In alternative embodiments, biomineralizations 160 may form as a result of mineralization of any tissue. For example, biomineralizations 160 may include atheromatous or other calcium-containing plaque (e.g., dental plaque), biliary stone, blood clot, a calcified tissue or plaque, or a cancerous tumor. Furthermore, biomineralizations 160 can be found within or outside of the body of a patient.

Turning back to the system 100 provided in FIG. 1, the synthetic cavitation nuclei 170 accumulate at surfaces of the biomineralizations 160. As referred to herein, "synthetic cavitation nuclei" are microbubbles. Specifically, each synthetic cavitation nucleus comprises an outer shell surrounding a core. In some embodiments, the outer shell comprises bio-lipids, proteins (e.g., albumin), surfactants, biocompatible polymers, or any combination thereof. In some embodiments, the core comprises a fluid. The fluid can be a low boiling-temperature fluid, such that the fluid is a gas at body temperature.

The synthetic cavitation nuclei are sized to diffuse quickly within aqueous fluids (e.g., urine) located within portions of a patient's body (e.g., ureters) in which pathological biomineralizations may be located. In certain embodiments, each of the synthetic cavitation nuclei have a baseline mean diameter (e.g., a diameter in the absence of a significantly elevated or diminished local pressure) of about 1 micron. Furthermore, the synthetic cavitation nuclei can undergo large-amplitude expansion and contraction upon experiencing longitudinal acoustic waves with peak pressures of about 1 megapascal. Such expansion and contraction of the synthetic cavitation nuclei can result in cavitation of the synthetic nuclei, thereby fragmenting an adjacent or nearby mass such as a biomineralization.

In certain embodiments, the synthetic cavitation nuclei have affinity for biomineralizations such that, when introduced into a portion of a patient's anatomy at which biomineralizations are located, the synthetic cavitation nuclei accumulate at surfaces of the biomineralizations. Specifically, in certain embodiments, the outer shell of each synthetic cavitation nucleus can include a targeting moiety having an affinity to biomineralizations, and thereby causing the synthetic cavitation nucleus to accumulate at surfaces of the biomineralizations. In particular, formation of chemical (e.g., covalent) bonds between the targeting moiety of the synthetic cavitation nucleus and a chemical constituent of the biomineralizations can cause the synthetic cavitation nucleus to accumulate at surfaces of the biomineralizations. Many biomineralizations that form within the human body contain calcium (e.g., calcium carbonate, calcium oxalate, calcium phosphate, or hydroxyapatite) and/or other metals. Thus targeting moieties can be selected to target metal- or calcium-containing biomineralizations. For example, synthetic pyrophosphonate analogs are one such moiety particularly useful for calcium-containing materials, and embodiments comprising synthetic pyrophosphate analogs are preferred embodiments of the present invention.

Other mechanisms such as surface tension can also facilitate accumulation at a treatment site. In some embodiments, the synthetic cavitation nuclei can be in proximity to, but not attached to, the biomineralizations.

Delivery of synthetic cavitation nuclei into or near the targeted mass, tissue, tumor, stone, bone or other site of interest can be achieved by a variety of means, as appropriate for the disease pathology and for the medical procedure being performed. For instance, in some embodiments, an aqueous suspension can be prepared containing the synthetic cavitation nuclei. The composition of the suspension can be chosen to facilitate use in the medical procedure. For example, in some embodiments the suspension can be water or some other physiological fluid. As used herein, the term "physiological fluid" refers to a fluid of the body, for example, including blood, lymph fluid, saliva, bile, urine, and interstitial fluid.

In some embodiments, synthetic cavitation nuclei are introduced to the blood, bile, urine, or cerebral spinal fluid. In some embodiments, synthetic cavitation nuclei are introduced to organs by percutaneous injection. In some embodiments, synthetic cavitation nuclei are introduced via an orifice of the body. Orifices include any opening such as the mouth, nose, eyes, vagina, urethra, and ears. In some embodiments, synthetic cavitation nuclei are introduced under the skin.

As a specific example, in some embodiments in which synthetic cavitation nucleic are to be placed in a ureter of a patient, a suspension of synthetic cavitation nuclei can be introduced into the ureter of the patient via a 5 Fr catheter. In such embodiments, a suspension with viscosity similar to water can be prepared such that the suspension easily flows through the 5 FR catheter. Using a cystoscope, the catheter can be easily positioned in the ureter of a patient and the suspension of synthetic cavitation nuclei can be introduced from a syringe attached to the catheter.

As another example, a suspension of synthetic cavitation nuclei can be prepared with a specific pH to coincide with the pH of an organ system in which the synthetic cavitation nuclei are to be placed. Suspensions can be also prepared with salts or other constituents to minimize aggregation of synthetic cavitation nuclei.

In some embodiments, synthetic cavitation nuclei are introduced directly at the treatment site, such as by direct implantation into a tissue or mass to be treated. In some such cases, the incorporation of targeting moieties into the shells of synthetic cavitation nuclei may be unnecessary. In other embodiments, synthetic cavitation nuclei are introduced at a location remote from the biomineralization to be treated (e.g., into the bloodstream via percutaneous injection) and travel to the treatment site.

In each of these methods it will be appreciated that synthetic cavitation nuclei can be introduced as part of a pharmaceutical formulation which may include, for example, solvents or other carriers, additives (e.g., stabilizers and preservatives, colorants, surfactants, pH-modifiers, etc.), and/or one or more pharmaceutically active agents.

Manufacture and delivery of synthetic cavitation nuclei is well known in the art and is described in many publications, including U.S. Pat. No. 10,149,906.

Turning once again back to FIG. 1, the ultrasound transducer assembly 140 is located with respect to the patient's torso 110 such that the ultrasound transducer assembly 140 is capable of producing the frustum-shaped beam 150.

The ultrasound transducer assembly 140 is a portion of an ultrasound device from which the ultrasonic beam 150 is emitted. In some embodiments, the ultrasound device includes further components in addition to the ultrasound transducer assembly 140. For example, in some embodiments, the ultrasound device can also include a console and/or a holster. In some embodiments, the console can further include a multi-channel amplifier circuit. Such embodiments are discussed in greater detail with regard to FIGS. 2 and 3.

Figure 2:
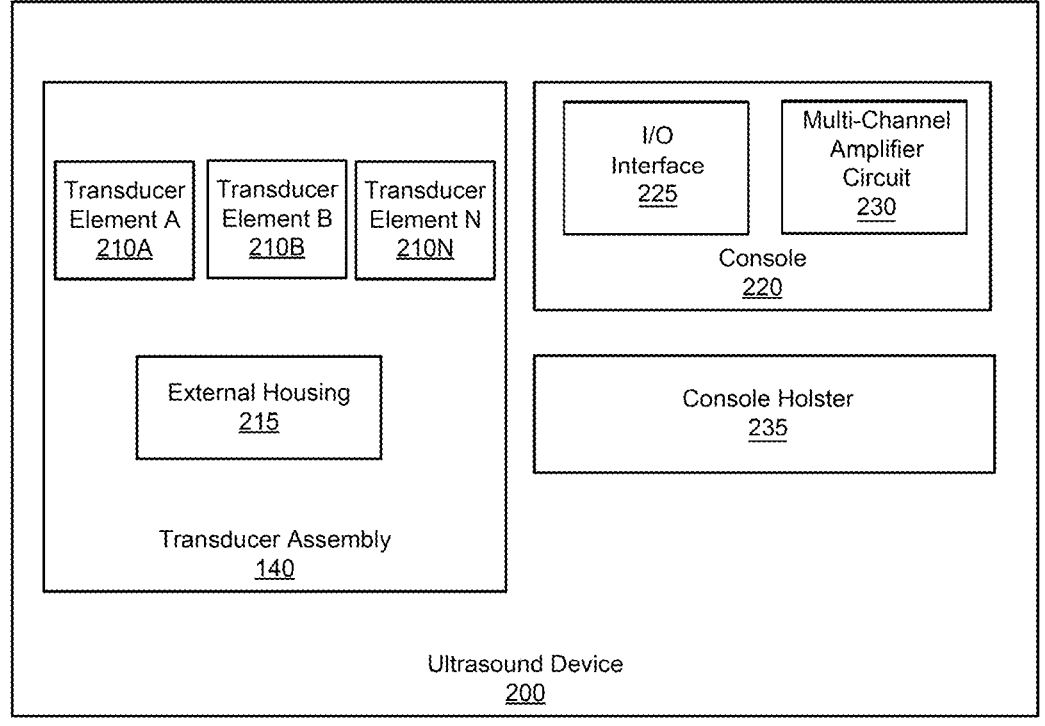
FIG. 2 is a block diagram of an ultrasound device, in accordance with an embodiment.

The ultrasound transducer assembly 140 includes a plurality of transducer elements (shown in FIG. 2). In some embodiments, the plurality of transducer elements are piezoelectric transducers. In alternative embodiments, the plurality of transducer elements can be capacitive micromachined elements. In some further embodiments, distinct subsets of one or more of the plurality of transducer elements are each actuated by one channel of a multi-channel amplifier circuit. In other words, each channel of a multi-channel amplifier circuit actuates a distinct subset including one or more of the plurality of transducer elements. Each ultrasound transducer element belongs to only one distinct subset. In certain embodiments, a multi-channel amplifier circuit comprises four channels. In some embodiments, each channel of a multi-channel amplifier circuit is associated with a subset comprising one of the plurality of transducer elements. In alternative embodiments, each channel of a multi-channel amplifier circuit is associated with a subset comprising two of the plurality of transducer elements.

At a given point in time, the multi-channel amplifier circuit is configured to operate in one of a plurality of states. Each state of the plurality of states in which the multi-channel amplifier circuit operates comprises a set of frequencies. Each set of frequencies (e.g., each state) includes a frequency at which each channel of the multi-channel amplifier circuit is configured to actuate its associated subset of ultrasound transducer elements. In some embodiments, a state in which the multi-channel amplifier circuit operates can comprise an "off-state." An off-state of the multi-channel amplifier circuit is defined by all channels of the multi-channel amplifier circuit actuating the associated subsets of ultrasound transducer elements at a frequency of 0 hertz. In alternative embodiments, a state in which the multi-channel amplifier circuit operates may comprise an "on-state" such that one or more channels of the multi-channel amplifier circuit actuate the one or more associated subsets of ultrasound transducer elements at a frequency of greater than 0 hertz. In an on-state, each of the channels of the multi-channel amplifier circuit can actuate its associated subset of ultrasound transducer elements at any frequency. For example, in an on-state, each of the channels of the multi-channel amplifier circuit can actuate its associated subset of ultrasound transducer elements at a distinct frequency. In other words, in an on-state, a frequency at which each channel of the multi-channel amplifier circuit actuates its associated subset of ultrasound transducer elements can differ from the other frequencies at which the other channels of the multi-channel amplifier circuit actuate the other associated subsets of ultrasound transducer elements.

Additionally, the multi-channel amplifier circuit can switch between states over a given time period. For example, the multi-channel amplifier circuit can switch from an on-state to an off-state during one cycle. In such embodiments, a ratio of the duration of an on-state to the duration of an off-state (also referred to herein as a "duty cycle") can be 0.05 (e.g., 5%). In some further embodiments, a sum of the durations of an on-state and an off-state (also referred to herein as a "cycle duration") can be less than 100 milliseconds but greater than 1 millisecond. It has been experimentally determined that, with peak pressures of an ultrasonic beam greater than 1 megapascal, a duty cycle of about 5% and a cycle duration of less than 100 milliseconds enables maintenance of a temperature of a patient's skin and muscle insonated by the beam within a few degrees Celsius of normal body temperature. Conversely, higher duty cycles or cycle durations greater than 100 milliseconds can result in heating of a patient's skin and muscle that is insonated by the beam, to temperatures at which injury can occur. Conversely, cycle durations less than 1 millisecond can be insufficient to generate a frustum-shaped beam.

In a particular embodiment, a multi-channel amplifier circuit can comprise four channels and the four channels can actuate the associated subsets of transducer elements at 466 kHz, 533 kHz, 500 kHz, and 566 kHz during a first cycle, then at 433 kHz, 566 kHz, 466 kHz, and 600 kHz during a second cycle, then at 400 kHz, 600 kHz, 433 kHz, and 566 kHz during a third cycle, and then at similar sets of frequencies during each of four additional cycles, for a total of seven cycles. These seven cycles can then repeat for a given duration of time.

The technique of switching states, and thus frequencies, of the plurality of transducer elements is an example of what is referred to in the art as "frequency modulation." As described in further detail below, the multi-channel amplifier circuit is capable of switching between states such that the resulting frequency modulation of the plurality of ultrasound transducer elements produces a frustum-shaped beam, such as the frustum-shaped beam 150 depicted in FIG. 1.

As referred to herein, a "frustum-shaped beam" comprises a frustum-shaped volume comprising a plurality of longitudinal acoustic waves, each longitudinal acoustic wave of the plurality of longitudinal acoustic waves produced by one of the plurality of ultrasound transducer elements, and the constructive and destructive interference of the longitudinal acoustic waves yielding approximately uniform peak pressures throughout a frustum-shaped volume, when the beam is located within water or another medium having a comparable, uniform density. As referred to herein, a "peak pressure" with regard to a frustum-shaped beam, refers to a minimum or maximum value of pressure of the longitudinal acoustic waves within the volume of the frustum-shaped beam. Furthermore, as referred to herein, "approximately uniform peak pressures" with regard to a frustum-shaped beam, refers to peak pressures of the longitudinal acoustic waves within the volume of the frustum-shaped beam being within 50% of a global maximum peak pressure of the longitudinal acoustic waves within the volume of the frustum-shaped beam. In some embodiments, the frequency and amplitude of the longitudinal acoustic waves comprising the frustum-shaped beam can vary over time, such that peak pressures of the frustum-shaped beam are between 0.5 megapascals and 10 megapascals, when measured in water.

The definition of a frustum-shaped beam used throughout this disclosure is dependent upon the medium through which the beam travels. Specifically, it should be assumed that frustum-shaped beams discussed throughout this disclosure travel through a medium having a uniform density that is known to those skilled in the art to be similar to the density of water. For example, for the purposes of this disclosure, muscle tissue can be considered to have a uniform density that is known to those skilled in the art to be similar to the density of water. On the other hand, mediums such as bony tissue are not considered to have a uniform density that is known to those skilled in the art to be similar to the density of water. Mediums such as bony tissue that do not have a uniform density similar to water can result in ultrasonic waves not having uniform peak pressures throughout the given volume. Therefore, ultrasonic waves that that travel through mediums that do not have a uniform density similar to water (e.g., bony tissue), are not considered to be frustum-shaped beams as referred to throughout this disclosure.

The frustum-shaped volume of a frustum-shaped beam 150 includes a first frustum base, a second frustum base, and a first distance between the first frustum base and the second frustum base. In certain embodiments, the first frustum base is located a second distance from a from a surface of the ultrasound transducer assembly 140 from which the plurality of ultrasound transducer elements produce the frustum-shaped beam 150. Geometry of the frustum-shaped beam 150 is described in greater detail with regard to FIG. 10.

The frustum-shaped beam 150 is capable of insonating a region of a patient's anatomy. In particular, in embodiments provided herein, the frustum-shaped beam 150 can be capable of insonating a large portion of a patient's ureter. Specifically, in embodiments in which the frustum-shaped beam 150 is used to insonate a ureter of a patient, the volume encompassed by the frustum-shaped beam 150 is similar to the volume encompassed by the patient's ureter, thereby enabling the frustum-shaped beam 150 to insonate a large portion of the ureter at one point in time. For instance, in some embodiments, the frustum-shaped beam 150 can insonate up to 10 cm of the length of a patient's ureter at one point in time. Furthermore, the frustum-shaped beam 150 can insonate a region located up to 13 cm from a surface of the ultrasound transducer assembly 140 from which the frustum-shaped beam 150 is produced. In further embodiments, the frustum-shaped beam 150 is capable of insonating the ureter of a patient with a body-mass index less than or equal to 40.

By insonating such a large portion of the patient's anatomy using the frustum-shaped beam 150, a plurality of biomineralizations can be treated simultaneously, as seen in FIG. 1. Furthermore, because the frustum-shaped beam 150 covers such a large portion of the patient's anatomy, even biomineralizations that are moving during the treatment process can be successfully insonated. The breadth and width of the frustum-shaped beam 150 can also allow treatment without the use of real-time imaging. Instead, basic knowledge of bony landmarks and other anatomy, in some embodiments accompanied by an imaging diagnostic performed prior to the procedure, can be sufficient to position the ultrasound transducer assembly 140 such that the frustum-shaped beam 150 is able to successfully insonate the portion of a patient's anatomy where the biomineralization is located. While a patient's respiration can cause movement of a biomineralization, in some embodiments, the biomineralization can be insonated without sedation of the patient due to the breadth and width of the frustum-shaped beam 150. In alternative embodiments, the patient may be sedated during insonation of a biomineralization. Placement of the ultrasound transducer assembly 140 with respect to the body of the patient for insonation is described in greater detail with regard to FIGS. 9 and 13 below.

Insonation of the synthetic cavitation nuclei 170 can cause cavitation of the synthetic cavitation nuclei 170. Cavitation of the synthetic cavitation nuclei 170 in proximity to the biomineralizations 160 can cause the delivery of energy to the proximal biomineralizations 160. This delivery of energy as a result of cavitation of the synthetic cavitation nuclei 170 can cause the biomineralizations 160 to fragment into smaller pieces such that may the fragmented biomineralizations can be removed from the patient or can pass from the patient via normal biological processes, such as urination.

In some embodiments in which a biomineralization comprises a biological entity such as a tissue or cell, cavitation of the synthetic cavitation nuclei 170 in proximity to the biological entity can cause destruction of the biological entity and/or disruption of biological processes involving the biological entity. In further embodiments in which a biomineralization comprises a biological entity such as a tissue or cell, cavitation of the synthetic cavitation nuclei 170 in proximity to the biological entity can mitigate calcification-associated stiffness of the biological entity, and/or cause other changes in mechanical properties of the biological entity.

As mentioned above, frustum-shaped beams exhibit approximate uniformity of peak pressures throughout the volume of the frustum-shaped beam. This approximate spatial uniformity of peak pressures has advantages for therapeutic use. For example, the approximate uniformity can be associated with favorable uniformity of a treatment effect. Additionally, the approximate spatial uniformity of peak pressures can enable approximately uniform distribution of peak negative pressure throughout the volume of the frustum-shaped beam. Peak negative pressure can help to expand synthetic cavitation nuclei to a large maximum radius in proportion to peak negative amplitude. Energy absorbed by the synthetic cavitation nuclei during such expansion can cause fragmentation of nearby biomineralizations during subsequent collapse of the synthetic cavitation nuclei as described above.

Devices

FIG. 2 is a block diagram of an ultrasound device 200, in accordance with an embodiment. The ultrasound device 200 shown in FIG. 2 includes the transducer assembly 140 of FIG. 1, in addition to a console 220 and a console holster 235. The transducer assembly 140 includes a plurality of transducer elements 210A-N and an external housing 215. The console 220 includes an I/O interface 225 and a multi-channel amplifier circuit 230. Some embodiments of the ultrasound device 200 have different components than those described here. Similarly, in some cases, functions can be distributed among the components in a different manner than is described here. For example, in some alternative embodiments, the multi-channel amplifier circuit 230 can be contained within the transducer assembly 140 as opposed to the console 220.

The transducer assembly 140 includes the plurality of transducer elements 210A-N. In some embodiments, each transducer element of the plurality of transducer elements 210A-N is a piezoelectric transducer. In alternative embodiments, each transducer element of the plurality of transducer elements 210A-N can be a capacitive micromachined element. The total number and size of transducer elements 210A-N depends upon the desired volume of the frustum-shaped beam produced by the transducer assembly 140. Specifically, the tradeoff between using a relatively small quantity of larger transducer elements of to produce greater efficiency of energy intensity, and using a relatively greater quantity of smaller transducer elements of to produce a more uniform pressure distribution across space, can be manipulated to select an optimal size and number of the transducer elements 210A-N. Based on experimental results, the optimal number of transducer elements 210A-N within the transducer assembly 140 is between four and eight, and the optimal size of the apertures of the transducer elements 210A-N is between 0.3 cm and 1.5 cm. The preferred embodiment of the transducer assembly 140 contains exactly four transducer elements 210A-N, each with an aperture size of 0.8 cm. Under these constraints, the transducer assembly 140 is capable of producing a beam with sufficient peak pressure uniformity, while still maintaining sufficient efficiency of energy intensity.

As described above, each transducer element of the plurality of transducer elements 210A-N can belong to a particular subset of a plurality of subsets of the transducer elements 210A-N. In some embodiments, each transducer element belongs to only one subset of the plurality of subsets. A subset of transducer elements can include one or more transducer elements 210A-N. Each subset of transducer elements can be operated independently of the other subsets of transducer elements. Specifically, each subset of transducer elements can operate at a frequency that differs from the frequencies at which the other subsets of transducer elements operate.

The frequency at which each subset of transducer elements operates is determined at least in part by the multi-channel amplifier circuit 230, which can receive input from a programmer of the ultrasound device 100 and/or from a user of the ultrasound device 200. The frequencies at which the multi-channel amplifier circuit 230 actuates each subset of transducer elements are discussed in greater detail below.

In addition to the plurality of transducer elements 210A-N, the transducer assembly 140 also includes the external housing 215. The external housing 215 is a cover or casing that holds the plurality of transducer elements 210A-N. The transducer assembly 140 also includes a surface from which the plurality of transducer elements 210A-N can emit the frustum-shaped beam.

As mentioned above, the console 220 includes the multi-channel amplifier circuit 230, which controls the output of the plurality of transducer elements 210A-N based on operational instructions received by the console 220 from a user of the device. In some embodiments, operational instructions can be input into the console 220 by the user via the I/O interface 225 included in the console 220. In other embodiments, instructions can be sent to the console 220 remotely via a wireless connection. Instructions provided to the console 220 can include a length of time of operation for the ultrasound device 200, one or more frequencies at which the ultrasound device 200 is to operate, or any additional instructions. Based on the received operational instructions, the multi-channel amplifier circuit 230 actuates the transducer assembly 140 accordingly.

The multi-channel amplifier circuit 230 comprises a plurality of channels. Each channel of the multi-channel amplifier circuit 230 is configured to actuate a distinct subset of transducer elements, as discussed above. Furthermore, at a given point in time, the multi-channel amplifier circuit 230 is configured to operate in one of a plurality of states. Each state of the plurality of states in which the multi-channel amplifier circuit 230 operates comprises a set of distinct frequencies. Each set of distinct frequencies (e.g., each state) includes a distinct frequency at which each channel of the multi-channel amplifier circuit 230 is configured to actuate its associated subset of ultrasound transducer elements. The multi-channel amplifier circuit 230 is configured to switch from one state to the next to produce a frustum-shaped beam based on instructions received via the console 220, which can in some embodiments be referred to herein as a "central processing unit".

In some embodiments, each channel of the multi-channel amplifier circuit 230 is associated with two transistors (e.g., MOSFETS). In such embodiments, the two transistors associated with each channel can control the frequency at which the channel actuates the distinct subset of ultrasound transducer elements associated with the channel, based on the state of the multi-amplifier circuit 230. In some embodiments, the two transistors associated with each channel can operate in an alternating manner, thereby causing the distinct subset of ultrasound transducer elements associated with the channel to produce an acoustic wave at a frequency between 100 kHz and 10,000 kHz based on the state of the multi-circuit amplifier 230, with about a 50% duty cycle, and about zero offset.

In some further embodiments, each channel of the multi-channel amplifier circuit 230 can be further associated with an electrical filter that can filter out high frequency components of the acoustic wave produced by the two transistors associated with the channel, thereby producing a sinusoidal wave.

In some embodiments, the multi-channel amplifier circuit 230 can include at least one power source to supply a constant voltage to the multi-channel amplifier circuit 230 throughout a duration of a state of the multi-channel amplifier circuit 230. In some embodiments, the at least one power source can further comprise at least two power sources. For example, the multi-channel amplifier circuit 230 can include 7 power sources.

In such embodiments in which the at least one power source further comprises at least two power sources, each of the at least two power sources can supply a distinct constant voltage to the multi-channel amplifier circuit 230 throughout a duration of a state of the multi-channel amplifier circuit 230. In other words, each of the at least two power sources can supply a different constant voltage to the multi-channel amplifier circuit 230 throughout a duration of a state of the multi-channel amplifier circuit 230. In such embodiments, each channel of the multi-channel amplifier circuit 230 can be associated with two transistors (e.g., MOSFETS), as described above. Additionally, the multi-channel amplifier circuit 230 can include at least one multiplexer. Each of the at least one multiplexers can serve to connect one of the at least two power sources to the two transistors associated with a channel of the multi-channel amplifier circuit 230. In such embodiments, each of the at least two power sources can further be a capacitor that is configured to charge to a sufficient level between states of the multi-channel amplifier circuit 230. For example, in some embodiments, each of the at least two power sources can further be a capacitor that is configured to charge at a charging rate of 21 kV/second.

In addition to receiving input from a user of the device, the I/O interface 225 of the console 220 can also serve as a mechanism for displaying the status of the ultrasound device 200 to users of the device. For example, the I/O interface 225 can indicate a status of operation of the transducer assembly 140. For instance, the I/O interface 225 can indicate whether the transducer assembly 140 is in an off-state or an on-state, as described above. Specific embodiments of the I/O interface 225 are discussed in greater detail with regard to FIG. 3.

In certain embodiments, a console holster 235 that is configured to contain the transducer assembly 140 can be attached to the console 220. In further embodiments, the transducer assembly 140 can be connected to the console 220 via a cord (shown in FIG. 3).

Figure 3:
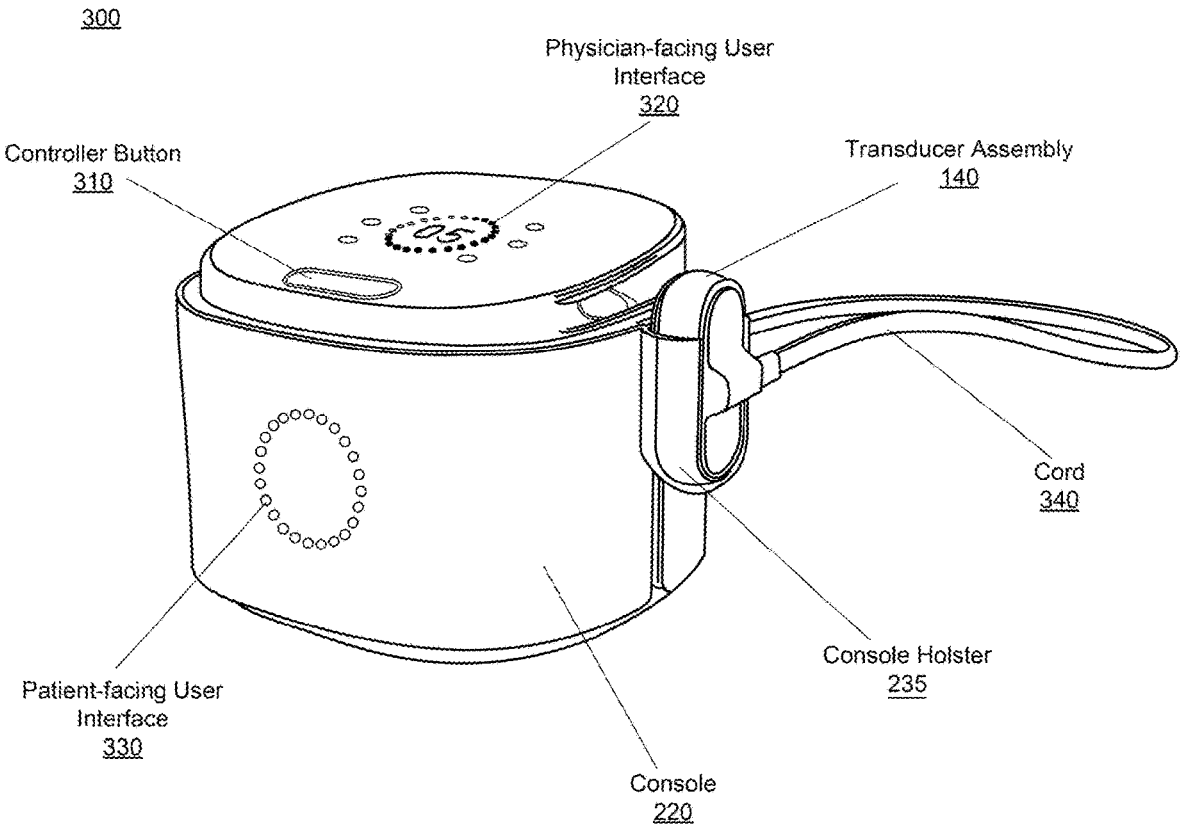
FIG. 3 is an illustration of an embodiment of the ultrasound device of FIG. 2.

FIG. 3 is an illustration of one embodiment 300 of the ultrasound device 200. The embodiment of the ultrasound device 300 includes the transducer assembly 140 of FIG. 1 and the console 220 and the console holster 235 of FIG. 2, in addition to a controller button 310, a physician-facing user interface 320, a patient-facing user interface 330, and a cord 340. Some embodiments of the ultrasound device 300 have different components than those described here. Similarly, in some cases, functions can be distributed among the components in a different manner than is described here.

The controller button 310 is a user interface through which a user of the ultrasound device 300 can provide actuation instructions to the ultrasound device 300. For example, in some embodiments, the controller button 310 can be a power button used to toggle the ultrasound device 300 on and off. In some embodiments the controller button 310 is located on the console 220.

The physician-facing user interface 320 and the patient-facing user interface 330 are two embodiments of the I/O interface 225 described with regard to FIG. 2. Specifically, the physician-facing user interface 320 and the patient-facing user interface 330 receive operational instructions from users of the device 300, and display the status of the actuation of the ultrasound device 300 to the users of the device. The physician-facing user interface 320 is positioned on the ultrasound device 300 such that it is visible to the physician operating the device. The patient-facing user interface 330 is positioned on the ultrasound device 300 such that it is visible to the patient receiving treatment via the device. The information displayed via the physician-facing user interface 320 and the patient-facing user interface 330 can be any type of information pertaining to the actuation and/or operation of the ultrasound device 300. For example, the interfaces 320 and 330 may display an indicator of the time remaining in the treatment.

The cord 340 connects the console 220 to the transducer assembly 140. As described above with regard to FIG. 2, the console 220 receives operational instructions for the ultrasound device 300 from a user of the device. In some embodiments, operational instructions for the ultrasound device 300 can also be transmitted wirelessly from a remote source. Based on the operational instructions received by the console 220, the multi-channel amplifier circuit 230 actuates the ultrasound transducer assembly 140.

As discussed above, in some embodiments, the multi-channel amplifier circuit 230 comprises one or more power sources (not shown in FIG. 3) that are configured to supply constant voltages to the multi-channel amplifier circuit 230 to actuate the transducer assembly 140. In some embodiments, the one or more power sources can be located within the console 220, such as batteries for example, or exterior to the console 220, such as from an external electricity source.

In embodiments in which the multi-channel amplifier circuit 230 is located within the console 220, power used to actuate the transducer assembly 140 can be transferred from the multi-channel amplifier circuit 230 within the console 220 to the transducer assembly 140 via the cord 340. In alternative embodiments, the multi-channel amplifier circuit 230 can be contained within the transducer assembly 140 as opposed to the console 220.

The console holster 235 is attached to the console 220, and is configured to hold the transducer assembly 140. In some embodiments, the console holster 235 is movable along the console 220 via a sliding mechanism. In further embodiments, the console holster 235 includes a gasket (not shown) that enables the transducer assembly 140 to securely and safely rest within the console holster 235.

Figure 4A:
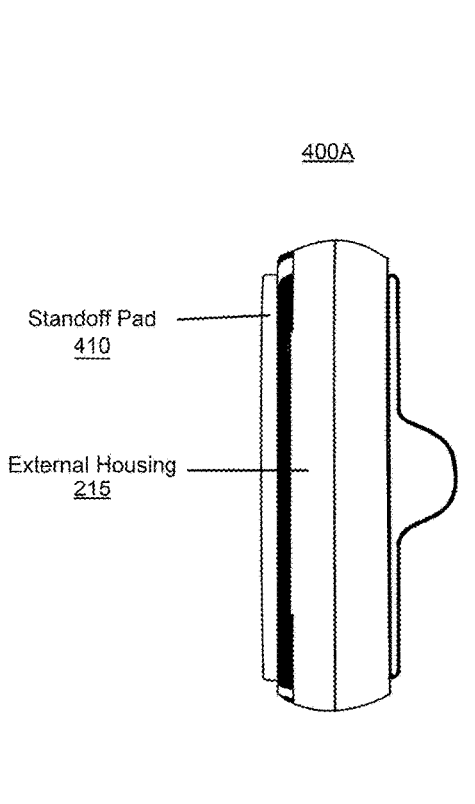
FIG. 4A is an illustration of an ultrasound transducer assembly, in accordance with an embodiment.

FIG. 4A is an illustration of a profile view 400A of the ultrasound transducer assembly 140, in accordance with an embodiment. The transducer assembly 400A includes at least the external housing 215 of FIG. 2. In some embodiments, the transducer assembly 400A also includes a standoff pad 410. Some embodiments of the transducer assembly 400A have different components than those described here. Similarly, in some cases, functions can be distributed among the components in a different manner than is described here.

The external housing 215 of FIG. 4A is one embodiment of the external housing 215 of FIG. 2. The external housing 215 is a cover or casing that holds the plurality of transducer elements 210A-N within the transducer assembly 400A. Two embodiments of the plurality of transducer elements 210A-N are shown in FIGS. 4B and 4C.

The standoff pad 410 of FIG. 4A is attached to a surface of the transducer assembly 400A from which the frustum-shaped beam is produced. In some embodiments, the standoff pad 410 comprises a gel-like material. In some embodiments, the standoff pad 410 further comprises an adhesive material that facilitates attachment of the standoff pad 410 to the surface of the transducer assembly 400A. In some embodiments, the standoff pad 410 is disposable and configured for single-use. In some embodiments, the standoff pad 410 comprises a material such that a frustum-shaped beam passing through the standoff pad 410 experiences attenuation that is similar to attenuation of the frustum-shaped beam passing through water.

The standoff pad 410 of FIG. 4A can act as a buffer between the surface of the transducer assembly 400A from which the frustum-shaped beam is produced, and an environment in which the transducer assembly 400A is located. In some embodiments, during use of the transducer assembly 400A for treatment of a patient, the standoff pad 410 is placed in contact with a treatment site on the body of the patient. In some embodiments, the standoff pad 410 includes a uniform (e.g., smooth) surface. In further embodiments, during use of the transducer assembly 400A to treat the patient, the uniform surface of the standoff pad 410 is placed in uniform contact with the treatment site on the body of the patient. In some embodiments, during treatment of the patient, an additional buffer material may be placed between the treatment site and the standoff pad 410. For example, an ultrasound gel may be placed between the treatment site and the standoff pad 410 during use of the transducer assembly 400A.

Figure 4B:
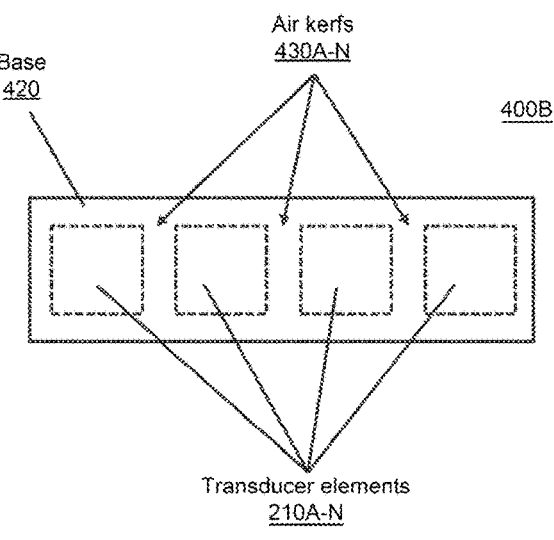
FIG. 4B is an illustration of a one-dimensional array of transducer elements, in accordance with an embodiment.
Figure 4C:
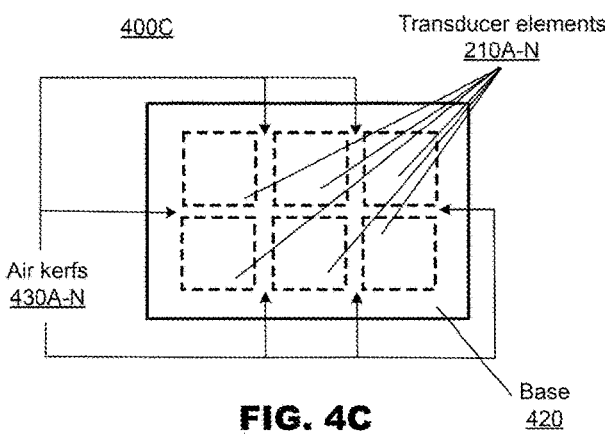
FIG. 4C is an illustration of a two-dimensional array of transducer elements, in accordance with an embodiment.

FIG. 4B is an illustration of a one-dimensional array of transducer elements 400B, in accordance with one embodiment. The array of transducer elements 400B includes the transducer elements 210A-N described in FIG. 2, a base 420, and air kerfs 430A-N. Some embodiments of the array of transducer elements 400B have different components than those described here. Similarly, in some cases, functions can be distributed among the components in a different manner than is described here.

The array of transducer elements 400B includes the transducer elements 210A-N. In certain embodiments, the transducer elements 210A-N in FIG. 4B are the transducer elements 210A-N discussed with regard to FIG. 2.

The base 420 is a platform for securing the transducer elements 210A-N. Specifically, the transducer elements 210A-N are fixed to the base 420 such that the surfaces of the transducer elements 210A-N that are distal to the base 420 are the portions of the transducer elements 210A-N that emit ultrasonic beams.

The base 420 is contained within the external housing 215 of FIG. 400A and oriented such that the beams emitted from the surfaces of the transducer elements 210A-N that are distal to the base 420 travel perpendicular to the standoff pad 410 in the direction of the standoff pad 410. Thus the base 420 is contained within the external housing 215 and oriented parallel to the standoff pad 410 such that the transducer elements 210A-N are located between the standoff pad 410 and the base 420.

The array of transducer elements 400B includes the transducer elements 210A-N arranged and fixed to the base 420 in a one-dimensional linear array. In alternative embodiments, an array of transducer elements may be arranged in any dimension. For example, as discussed with regard to FIG. 4C below, an array of transducer elements may be arranged in two-dimensions. Additionally, while the array of transducer elements 400B includes a total of four transducer elements 210A-N of the same size, in alternative embodiments, an array of transducer elements may contain any number and/or size of transducer elements. For example, in some embodiments, a transducer assembly can comprise at least 4 and at most 8 transducer elements. In certain further embodiments, one or more of the transducer elements is apodized.

In one embodiment, a space exists between each transducer element of the plurality of transducer elements 210A-N and the nearest neighbor. This space exists to enable each transducer element 210A-N to operate at a frequency independent of the frequencies of the other transducer elements in some embodiments.

In the embodiment depicted in FIG. 4B, the spaces between each transducer element and its nearest neighbor comprise the air kerfs 430A-N. In alternative embodiments, the space between transducer elements may be filled with any type of material.

In the embodiment depicted in FIG. 4B, the air kerfs 430A-N separate transducer elements by a distance of between 50 and 500 micrometers. In one preferred embodiment, the space between each transducer element and its nearest neighbor comprises an air kerf of about 100 micrometers. In another preferred embodiment, the space between each transducer element and its nearest neighbor comprises an air kerf of about 400 micrometers. In alternative embodiments, the spaces between transducer elements may separate the transducer elements by any distance.

In the embodiment depicted in FIG. 4B, the air kerfs 430A-N separate the transducer elements by the same distance. In alternative embodiments, the distances that separate the transducer elements may vary within a transducer assembly.

FIG. 4C is an illustration of a two-dimensional array of transducer elements 400C, in accordance with one embodiment. The array of transducer elements 400C includes the transducer elements 210A-N described in FIG. 2, and the base 420 and the air kerfs 430A-N described in FIG. 4B. Some embodiments of the array of transducer elements 400C have different components than those described here. Similarly, in some cases, functions can be distributed among the components in a different manner than is described here.

The array of transducer elements 400C includes the transducer elements 210A-N. In certain embodiments, the transducer elements 210A-N in FIG. 4B are the transducer elements 210A-N discussed with regard to FIGS. 2 and 4B.

The base 420 is a platform for securing the transducer elements 210A-N. In certain embodiments, the base 420 in FIG. 4B is the base 420 discussed with regard to FIG. 4B.

The array of transducer elements 400C includes the transducer elements 210A-N arranged and fixed to the base 420 in a two-dimensional array. The two-dimensional array includes a first distance and direction and a second distance and direction, and an angle between the first direction and the second direction. In one embodiment, the two-dimensional array extends between 50 millimeters and 150 millimeters in the first direction, extends between 20 millimeters and 60 millimeters in the second direction, and has the angle between the first direction and the second direction is between 45 and 120 degrees. In a preferred embodiment of the transducer assembly 140, the two-dimensional array of transducer elements 210A-N extends 100 millimeters in the first direction, extends 30 millimeters in the second direction, and the angle between the first direction and the second direction is 90 degrees. In an alternative embodiment, the two-dimensional array may have any alternative first distance, second distance, and angle.

As noted above, in alternative embodiments, an array of transducer elements 210A-N may be arranged in any dimension. Additionally, while the array of transducer elements 400C includes a total of six transducer elements 210A-N of the same size, in alternative embodiments, an array of transducer elements may contain any number and/or size of transducer elements. For example, in some embodiments, a transducer assembly can comprise at least 4 and at most 8 transducer elements. In certain further embodiments, one or more of the transducer elements is apodized.

Similar to FIG. 4B, FIG. 4C depicts a space comprising air kerfs 430A-N between each transducer element of the plurality of transducer elements 210A-N and the nearest neighbors. In some embodiments, the air kerfs 430A-N of FIG. 4C are the air kerfs 430A-N discussed with regard to FIG. 4B.

Figure 5:
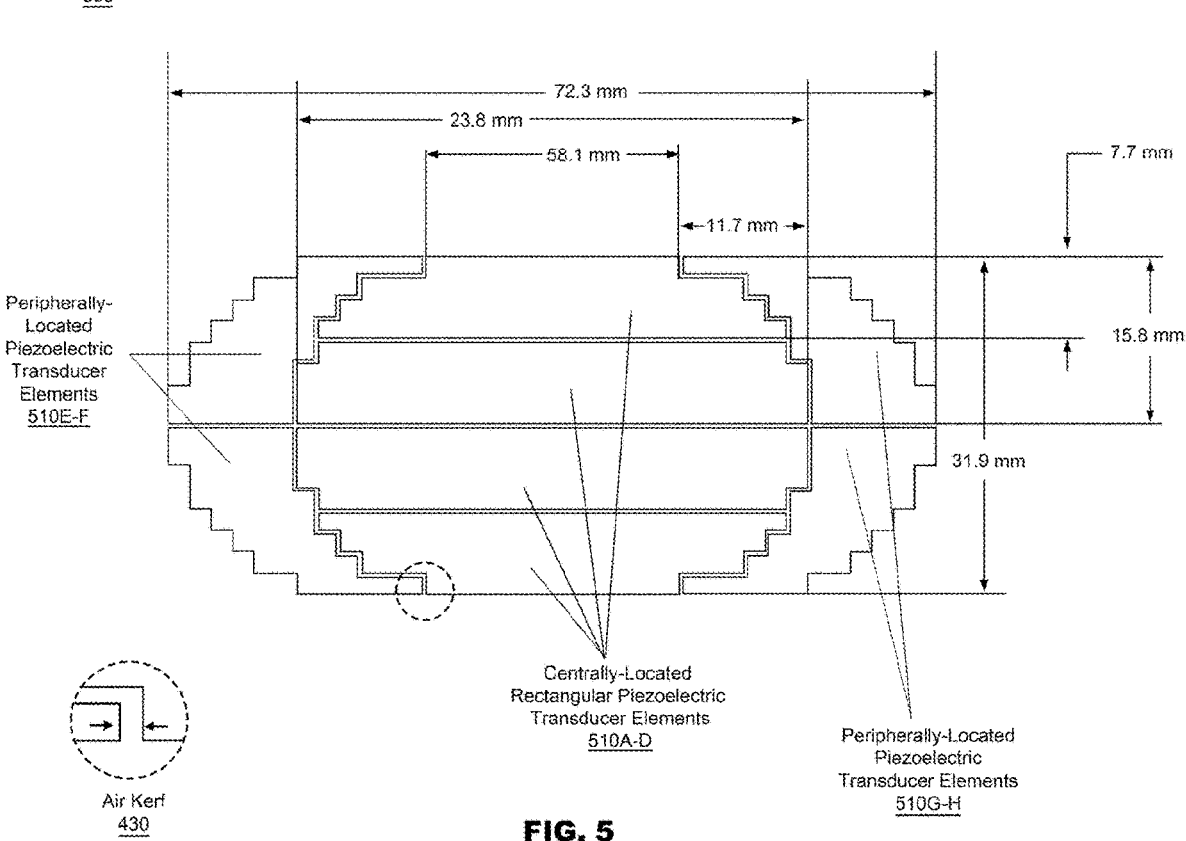
FIG. 5 illustrates a multi-element, piezoelectric ultrasound transducer assembly, in accordance with an embodiment.

FIG. 5 illustrates a multi-element, piezoelectric ultrasound transducer assembly 500, in accordance with an embodiment. The multi-element, piezoelectric ultrasound transducer assembly 500 is shown from above in FIG. 5. The multi-element, piezoelectric ultrasound transducer assembly 500 includes eight piezoelectric transducer elements 510A-H separated by air kerfs. As shown in FIG. 5, the piezoelectric transducer elements 510A-H are long elements arranged in a 1.5 dimensional array. Specifically, four centrally-located rectangular piezoelectric transducer elements 510A-D are flanked by four peripherally-located piezoelectric transducer elements 510E-H. Each peripherally-located piezoelectric transducer element 510E-H is electrically coupled to a centrally-located rectangular piezoelectric transducer element 510A-D through a modulation scheme, but is actuated with a relatively lower electrical current to achieve apodization. An exemplar air kerf 430 is shown magnified in FIG. 5.

Exemplar dimensions of the multi-element, piezoelectric ultrasound transducer assembly 500 are indicated in FIG. 5. The largest dimensions of the multi-element, piezoelectric ultrasound transducer assembly 500 depicted in FIG. 5 are 72.3 mm and 31.9 mm. The dimensions of the centrally-located rectangular piezoelectric transducer elements 510A-D are between 23.8 mm and 58.1 mm, and 7.7 mm. The dimensions of the peripherally-located piezoelectric transducer elements 510E-H are 11.7 mm and 15.8 mm. A width of the air kerf 430 is 0.4 mm. In alternative embodiments, the multi-element, piezoelectric ultrasound transducer assembly 500 can be defined by any alternative dimensions.

Figure 6:
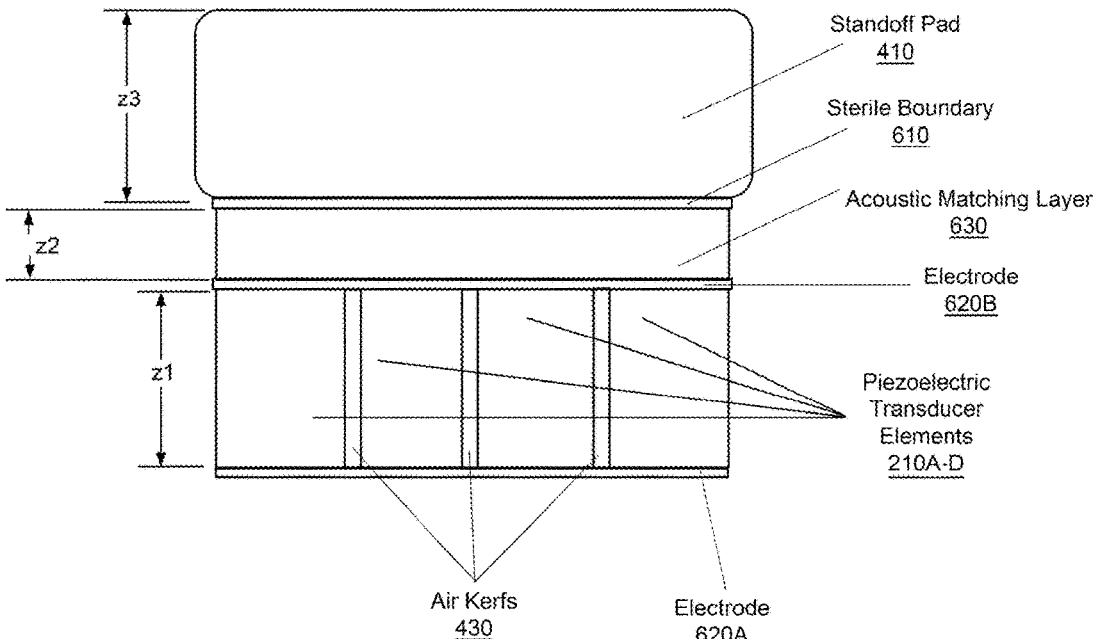
FIG. 6 illustrates cross-section of the piezoelectric ultrasound transducer assembly of FIG. 11B, in accordance with an embodiment.
Figures 11A, 11B:
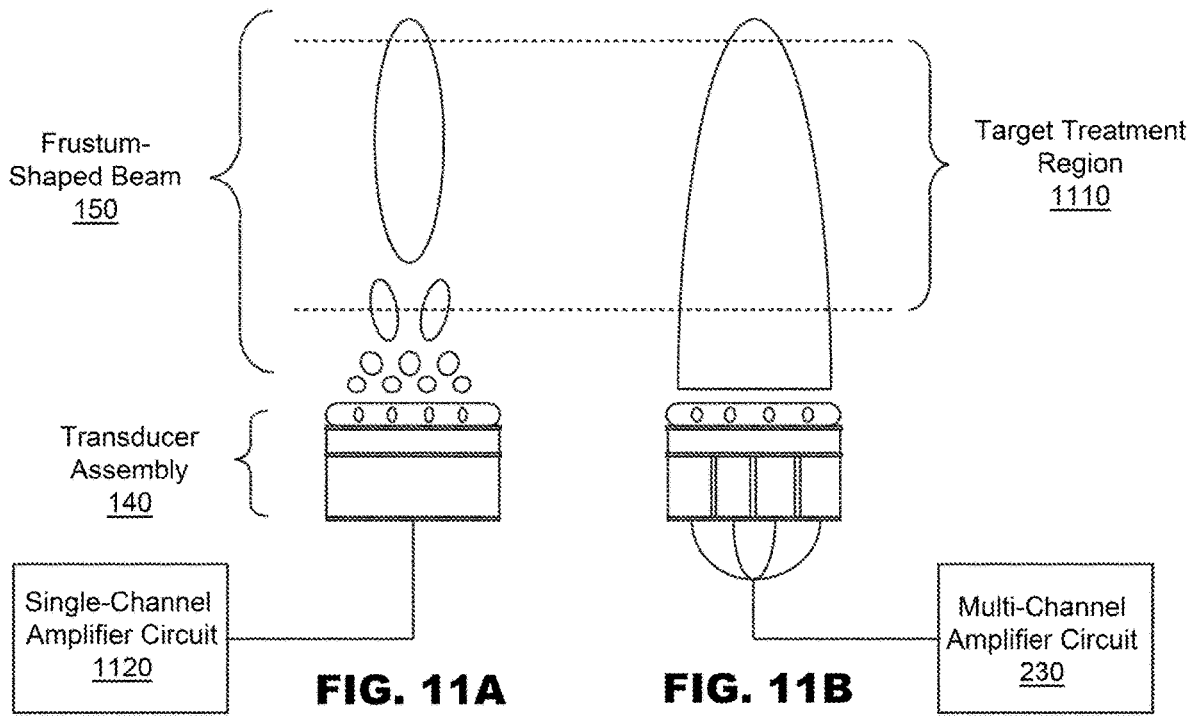
FIG. 11A illustrates a frustum-shaped beam produced by a transducer assembly actuated by a multi-channel amplifier circuit at single frequency, in accordance with an embodiment.
FIG. 11B illustrates a frustum-shaped beam produced by a transducer assembly actuated by a multi-channel amplifier circuit via a frequency modulation scheme, in accordance with an embodiment.

FIG. 6 illustrates a cross-section 600 of the piezoelectric ultrasound transducer assembly of FIG. 11B, in accordance with an embodiment. The cross-section 600 depicts four piezoelectric transducer elements 210A-D, separated from one another by air kerfs 430. The piezoelectric transducer elements 210A-D can comprise lead zirconate titanate (PZT). A height $z_1$ of each piezoelectric transducer element 210A-D can be about one wavelength. Existence of an even number of half-wavelengths for the heights $z_1$ of the piezoelectric transducer elements 210A-D can reduce the resonance of the piezoelectric ultrasound transducer assembly, and therefore broaden the frequency bandwidth available for frequency modulation.

The piezoelectric transducer elements 210A-D are located between two electrodes, electrodes 620A-B. The electrodes 620A-B can comprise thin plate or foil electrodes. The electrodes 620A-B are in communication with the multi-channel amplifier circuit 230, as discussed in further detail below, and are configured to actuate the piezoelectric transducer elements 210A-D.

The piezoelectric ultrasound transducer assembly depicted in FIG. 6 is fixed to an external housing (shown in FIG. 4A) via an acoustic matching layer 630 located adjacent to the electrode 620B. The acoustic matching layer 630 can comprise a material having an acoustic impedance between that of PZT and water. A height $z_2$ of the acoustic matching layer 630 can be about half of a wavelength. A standoff pad 410 can comprise a material having a law acoustic impedance, such as mineral oil, acoustic gel, or water, to minimize absorption and scattering of acoustic waves. The standoff pad 410 can have any height $z_3$. A sterile boundary 610 can be located between the acoustic matching layer 630 and the standoff pad 410. In certain embodiments, air or foam can be located beneath the electrode 620A to amplify acoustic reflections.

Figure 7:
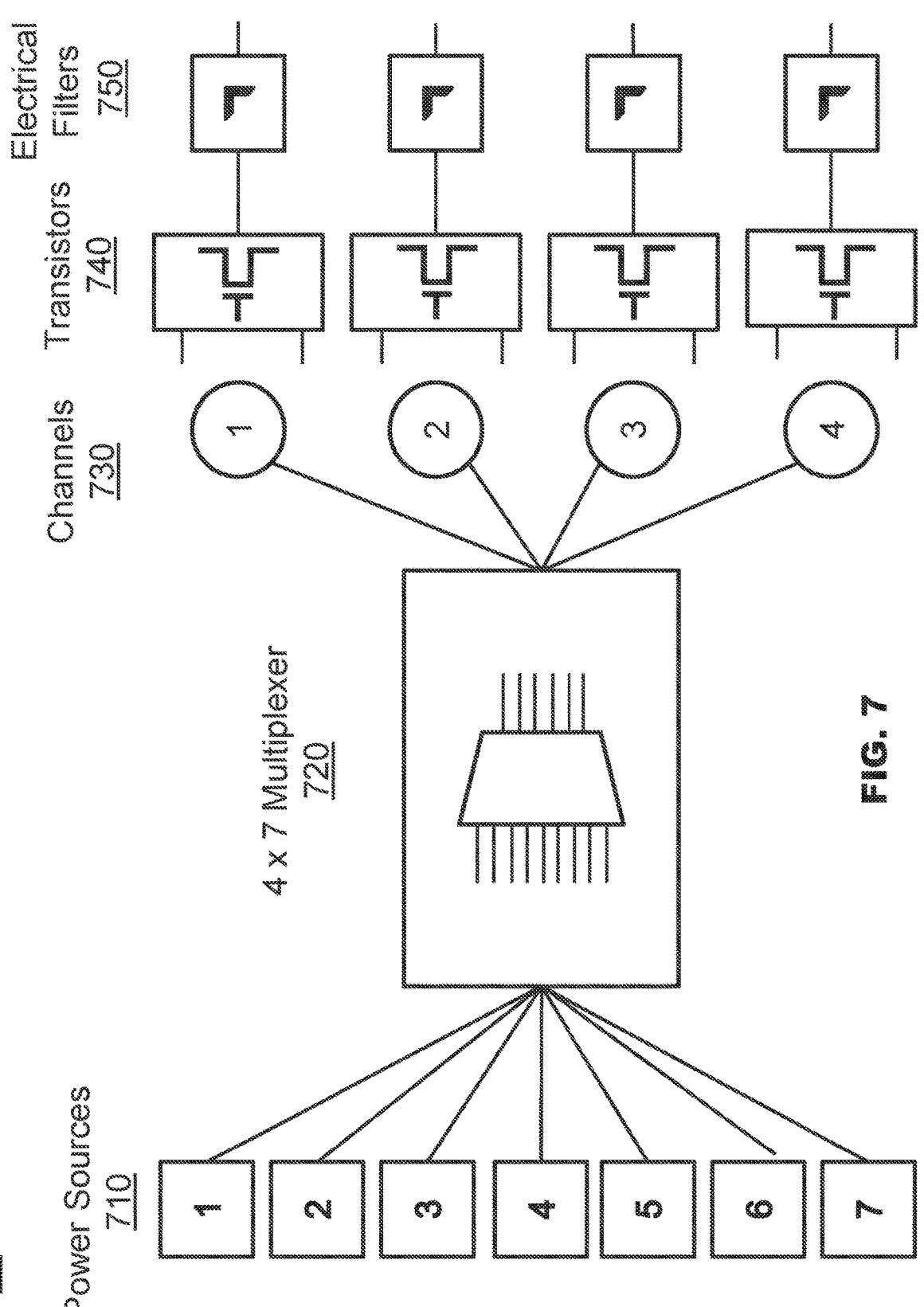
FIG. 7 is a block diagram of a multi-channel amplifier circuit, in accordance with an embodiment.

FIG. 7 is a block diagram of a multi-channel amplifier circuit 700, in accordance with an embodiment. The multi-channel amplifier circuit 700 depicted in FIG. 7 is one embodiment of the multi-channel amplifier circuit 230 described above with regard to FIG. 2. Alternative embodiments of the multi-channel amplifier circuit 230 can comprise additional or fewer components than the multi-channel amplifier circuit 700 depicted in FIG. 7.

As shown in FIG. 7, the multi-channel amplifier circuit 700 includes a plurality of power sources 710 configured to supply constant voltages to the multi-channel amplifier circuit 700. Specifically, each power source 710 is configured to supply a distinct constant voltage to the multi-channel amplifier circuit 700. In some embodiments, each of the power sources 710 can be a capacitor that is configured to charge at a charging rate such that each power source can reach a desired voltage during a period of time that is less than a duration of an off-state cycle of the multi-channel amplifier circuit 700. For example, in some embodiments, each of the power sources 710 can be a capacitor that is configured to charge at a charging rate of 21 kV/second. In the embodiment depicted in FIG. 7, the multi-channel amplifier circuit 700 includes 7 power sources 710. In alternative embodiments, the multi-channel amplifier circuit 700 can include any number of power sources.

As discussed above, a multi-channel amplifier circuit comprises a plurality of channels 730. For example, in the embodiment of the multi-channel amplifier circuit 700 depicted in FIG. 7, the multi-channel amplifier circuit 700 comprises 4 channels 730. In alternative embodiments, the multi-channel amplifier circuit 700 can comprise any quantity of channels 730. Each channel 730 of the multi-channel amplifier circuit 700 is configured to actuate a distinct subset of transducer elements.

In the embodiment depicted in FIG. 7, each channel 730 of the multi-channel amplifier circuit 700 is associated with two transistors 740. The transistors 740 can comprise MOS-FETS. In certain embodiments, the two transistors 740 associated with each channel 730 can control the frequency at which the channel 730 actuates the distinct subset of ultrasound transducer elements associated with the channel 730 based on the state of the multi-channel amplifier circuit 700. In some embodiments, the two transistors 740 associated with each channel 730 can operate in an alternating manner, thereby causing the distinct subset of ultrasound transducer elements associated with the channel 730 to produce an acoustic wave at a frequency between 100 kHz and 10,000 kHz based on the state of the multi-channel amplifier circuit 700, with about a 50% duty cycle, and about zero offset.

In the embodiment depicted in FIG. 7, each channel 730 of the multi-channel amplifier circuit 700 is further associated with an electrical filter 750 that can filter out high frequency components of the acoustic wave produced by the two transistors 740 associated with the channel, thereby producing a sinusoidal wave.

The multi-channel amplifier circuit 700 depicted in FIG. 7 also includes a multiplexer 720 that connects the power sources 710 to the transistors 740 and the filters 750 associated with each channel 730. Specifically, at a given point in time, the multiplexer 720 connects one or more of the power sources 710 to the transistors 740 and the filters 750 associated with each channel 730. Furthermore, the multiplexer 720 is capable of switching connections between the power sources 710 and the transistors 740 and filters 750 associated with each channel. Therefore, at different points in time, the power sources 710 can be differentially connected to the transistors 740 and the filters 750 associated with each channel 730.

In the embodiment depicted in FIG. 7, the multiplexer 720 comprises a 4×7 multiplexer because the multiplexer 720 connects 7 power sources 710 to the transistors 740 and filters 750 associated with 4 channels 730. However, as mentioned above, in alternative embodiments, the multi-channel amplifier circuit 700 can comprise any quantity of power sources 710 and channels 730. Thus, in alternative embodiments the multiplexer 720 can comprise a multiplexer with any number of input and output dimensions.

In some embodiments, at a given point in time, a single power source 710 is connected to the transistors 740 and filters 750 associated with a single channel 730. In other words, in some embodiments, there is a 1:1 connection between the power sources 710 and the channels 730. In alternative embodiments, more than one power source 710 can be connected to the transistors 740 and the filters 750 associated with each channel 730.

Figure 8:
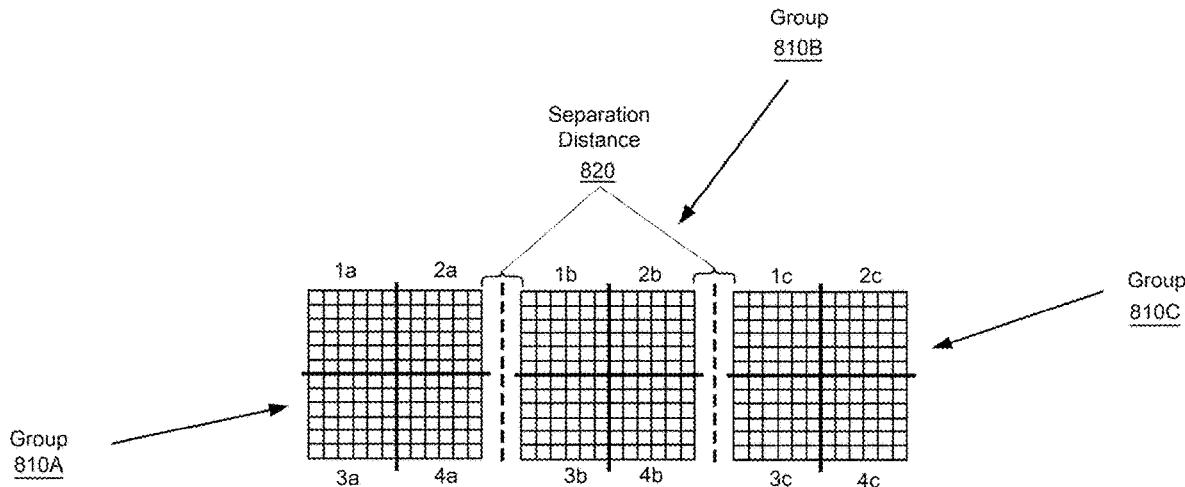
FIG. 8 illustrates an ultrasound transducer assembly, in accordance with an embodiment.

FIG. 8 illustrates an ultrasound transducer assembly 800, in accordance with an embodiment. The embodiment of the ultrasound transducer assembly 800 comprises three groups

810A-C of four transducer elements. As shown in FIG. 8, the group 810A comprises ultrasound transducer elements 1*a*, 2*a*, 3*a*, and 4*a*. The group 810B comprises ultrasound transducer elements 1*b*, 2*b*, 3*b*, and 4*b*. The group 810C comprises ultrasound transducer elements 1*c*, 2*c*, 3*c*, and 4*c*. Within each group of transducer elements 810 A-C, the four transducer elements can be separated by electrical insulators.

The groups of transducer elements 810A-C can be arranged in an array, and separated by separation distances 820, as shown in FIG. 8. In some embodiments, the separation distance 820 can be between 12.5 mm and 0 mm. In embodiments in which the separation distance 820 comprises 0 mm, an electrical insulator can be located between the groups of transducer elements 810A-C. In certain embodiments, groups of transducer elements located on an edge of the ultrasound transducer assembly 800 (e.g., the groups of transducer elements 810A and 810C) can be wound to a transformer to achieve apodization.

In an embodiment of the ultrasound transducer assembly 800, one or more of the transducer elements of the groups 810A-C can comprise sub-elements, depicted as squares in FIG. 8, and arranged in a grid pattern. In some embodiments, a transducer element can comprise of 36 sub-elements. Each sub-element can comprise dimensions of 2 mm×2 mm. Air kerfs having widths of about 100 micrometers can separate the sub-elements in a transducer element from one another.

The ultrasound transducer elements in the groups 801A-C can be actuated independently of one another. To actuate an ultrasound transducer element, the sub-elements of the ultrasound transducer element can be actuated in unison by a common electrode at any frequency. In some embodiments, one transducer element from each group 810A-C can be actuated at the same frequency. In further embodiments, this pattern of actuating one transducer element from each group 810A-C at the same frequency can be followed for all transducer elements in the groups 810A-C. For example, the transducer elements 1*a*, 1*b*, and 1*c* can be actuated at the same frequency, the transducer elements 2*a*, 2*b*, and 2*c* can be actuated at the same frequency, the transducer elements 3*a*, 3*b*, and 3*c* can be actuated at the same frequency, and the transducer elements 4*a*, 4*b*, and 4*c* can be actuated at the same frequency. In such embodiments, the resulting pressure distribution originating from the ultrasound transducer assembly 800 can comprise a frustum-shaped beam as described throughout this disclosure.

Figure 9:
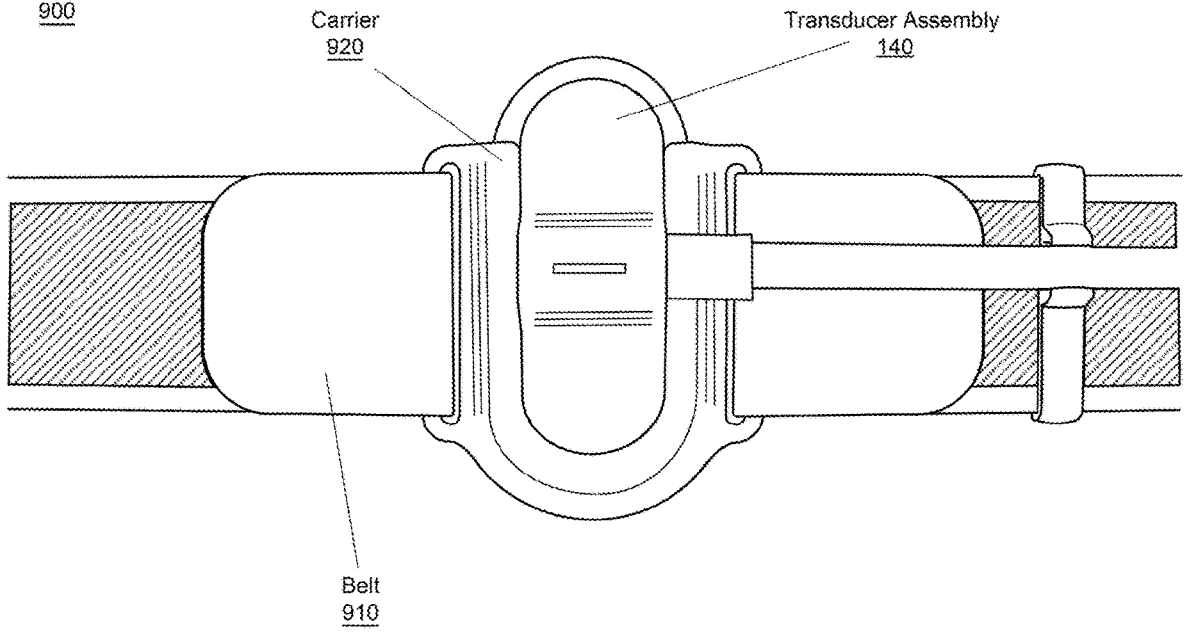
FIG. 9 is an illustration of a belt for use in performing a procedure using an ultrasound device, in accordance with an embodiment.

In certain embodiments, during treatment of a patient using the transducer assembly 140, the transducer assembly 140 may be held in place at a treatment site by a user of the device. However, this method of treatment may prove inefficient if the treatment duration extends over a long period of time. Additionally, it may be difficult to maintain a positioning of the transducer assembly 140 during treatment, which may compromise the efficacy of the treatment. Thus certain tools for securing the transducer assembly 140 to a treatment site may be utilized. FIG. 9 discloses one embodiment of such a tool.

FIG. 9 is an illustration of an ultrasound device belt 900, in accordance with an embodiment. In an embodiment, the ultrasound device belt 900 includes a belt 910, a carrier 920, and the transducer assembly 140. Some embodiments of the ultrasound device belt 900 have different components than those described here. Similarly, in some cases, functions can be distributed among the components in a different manner than is described here.

The belt 910 is a length of material configured to secure the a surface of the ultrasound transducer assembly 140 from which the frustum-shaped beam originates to a treatment site. The belt 910 may be made of any type of material and is adjustable such that it can be adapted to secure the transducer assembly 140 to a treatment site of any shape and/or size. For example, the belt 910 may include an adhesive material such as Velcro, such that the shape and size of the belt can be quickly and easily manipulated.

The carrier 920 is a receptacle that is connected to the belt 920 and is used to attach the ultrasound transducer assembly 140 to the belt 910. The carrier 920 holds the ultrasound transducer assembly 140 in place during treatment using the belt 910.

One embodiment of a method for using the ultrasound device belt 900 during treatment is discussed in further detail with regard to FIG. 14 below.

Frustum-Shaped Beam

Figure 10:
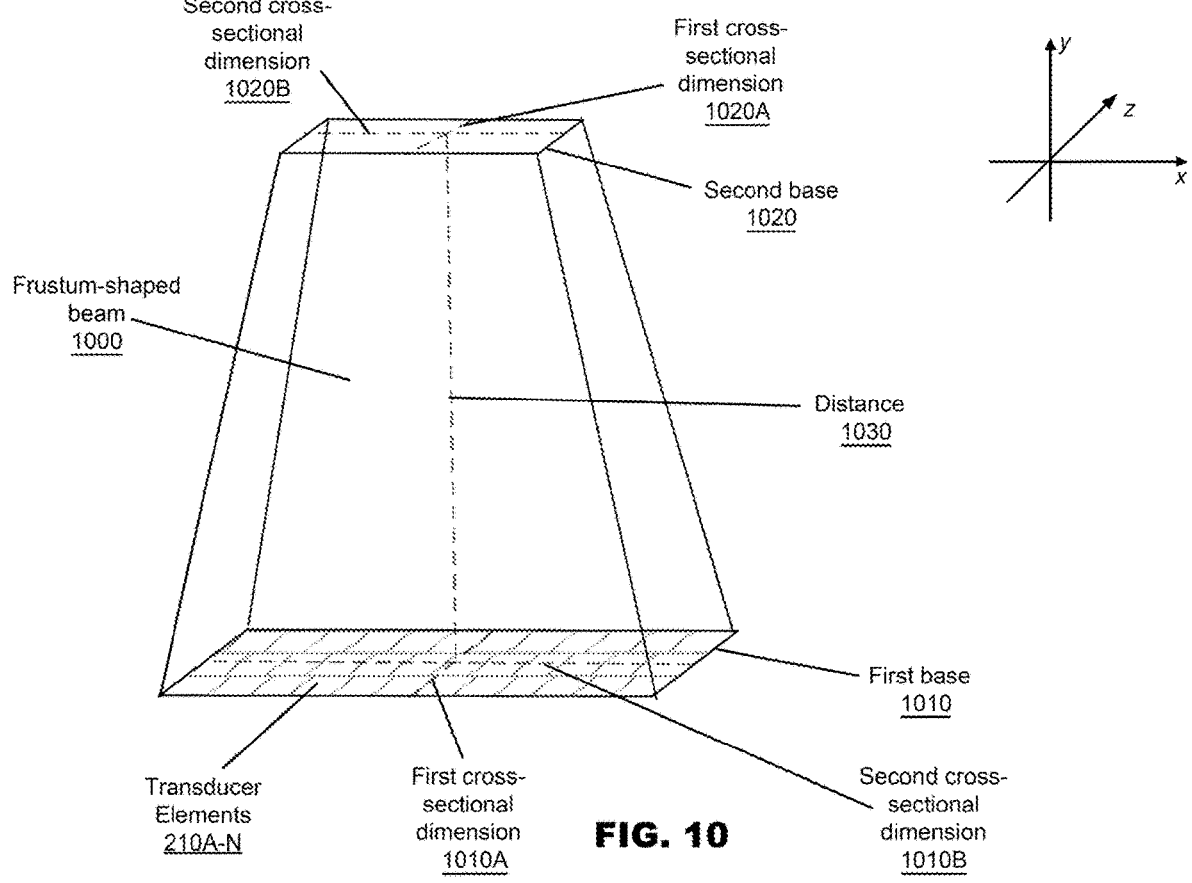
FIG. 10 is an illustration of a frustum-shaped beam, in accordance with an embodiment.

As described above in detail with regard to FIG. 1, the transducer assembly 140 is capable of generating a frustum-shaped beam. FIG. 10 is an illustration of a frustum-shaped beam 1000 emitted from the transducer elements 210A-N, in accordance with an embodiment. The transducer elements 210A-N are one embodiment of the transducer elements 210A-N discussed with regard to FIGS. 2-4C.

The frustum-shaped beam 1000 comprises a plurality of longitudinal acoustic waves having approximately spatially uniform peak pressures that insonate a volume of space defined as a frustum. As discussed in detail above, the approximate spatial uniformity of the peak pressures of the frustum-shaped beam 1000 is dependent upon the beam being located within water or another medium having a comparable, uniform density.

A frustum shape is obtained by intersecting a geometric volume that includes at least one base, with one or more planes parallel to the at least one base. A frustum may be based off of any geometric volume that includes at least one base. In the embodiment of the frustum-shaped beam 1000 depicted in FIG. 10, the frustum is a portion of a rectangular-base pyramid. Specifically, the frustum-shaped beam 1000 is the portion of a rectangular-base pyramid that remains after a superior portion of the pyramid has been intersected and removed by a plane parallel to the base of the pyramid. However, in alternative embodiments, the frustum-shaped beam 1000 may be based off of any 3-dimensional shape. For example, the frustum-shaped beam 1000 may be based off of a cone, a cylinder, or any other volume.

The frustum-shaped beam 1000 includes a first base 1010, a second base 1020, and a first distance 1030 between the first base 1010 and the second base 1020. The first base 1010 is located a second distance (not shown) from a surface of the ultrasound transducer assembly 140 from which the frustum-shaped beam 1000 is produced by the transducer elements 210A-N. In some embodiments, the second distance is about 2 cm. In alternative embodiments, the second distance is greater than or less than 2 cm. The second distance decreases as the quantity of transducer elements 210A-N increases. Furthermore, the first base 1010 and the second base 1020 are parallel to the faces of the transducer elements 210A-N. The first base 1010 comprises a first cross-sectional dimension 1010A and a second cross-sectional dimension 1010B. The second base 1020 also comprises a first cross-sectional dimension 1020A and a second cross-sectional dimension 1020B.

The dimensions of the frustum-shaped beam 1000 are such that the beam can insonate up to 10 cm of the length of a patient's ureter at one time and/or a ureter of a patient with a body-mass index less than or equal to 40. An area of the first frustum base 1010 is larger than an area of the second frustum base 1020 due to constructive and destructive interference effects of the longitudinal acoustic waves that comprise the frustum-shaped beam 1000. Additionally, by setting dimensions of the first base 1010, dimensions of the second base 1020 can be determined. With these specifications in mind, the first cross-sectional dimension 1010A of the first base 1010 of the beam 1000 is at least 2.5 centimeters and at most 5 centimeters. In one preferred embodiment, the first cross-sectional dimension 1010A of the first base 1010 of the beam 1000 is about 2.6 centimeters. In another preferred embodiment, the first cross-sectional dimension 1010A of the first base 1010 of the beam 1000 is about 3.2 centimeters. The second cross-sectional dimension 1010B of the first base 1010 of the beam 1000 is at least 5 centimeters and at most 10 centimeters. In a preferred embodiment, the second cross-sectional dimension 1010B of the first base 1010 of the beam 1000 is about 7.5 centimeters. In some embodiments, a shape of the first base 1010 comprises a square. The first cross-sectional dimension 1020A of the second base 1020 of the beam 1000 is at least 0 centimeters and at most 4 centimeters. In a preferred embodiment, the first cross-sectional dimension 1020A of the second base 1020 of the beam 1000 is at about 0 centimeters, such that the second base 1020 is a one-dimensional line. The second cross-sectional dimension 1020B of the second base 1020 of the beam 1000 is at least 1 centimeters and at most 15 centimeters. In one preferred embodiment, the second cross-sectional dimension 1020B of the second base 1020 of the beam 1000 is about 2 centimeters. In another preferred embodiment, the second cross-sectional dimension 1020B of the second base 1020 of the beam 1000 is about 10 centimeters. Finally, the distance first 1030 between the first base 1010 and the second base 1020 is at least 12 centimeters and at most 20 centimeters. In a preferred embodiment, the first distance 1030 is about 14 centimeters.

Note that FIG. 10 is only one embodiment of a volume that may be insonated by the transducer elements 210A-N. Alternative embodiments of beam volumes not explicitly disclosed herein are also possible.

FIG. 11A illustrates a frustum-shaped beam 150 produced by a transducer assembly 140 actuated by a single-channel amplifier circuit 1120, in accordance with an embodiment. In contrast, FIG. 11B illustrates a frustum-shaped beam 150 produced by a transducer assembly 140 actuated by a multi-channel amplifier circuit 230 via a frequency modulation scheme, in accordance with an embodiment.

A region that is proximal to a transducer assembly 140 is referred to as the near field. Conversely, a region that is distal to a transducer assembly 140 is referred to as the far field. Treatment of a patient using a transducer assembly 140 occurs primarily in the far field. A target treatment region 1110 for the frustum-shaped beam 150 is depicted in both FIGS. 11A and 11B. In some embodiments, the target treatment region 1110 for the frustum-shaped beam 150 extends between 5 and 15 centimeters.

The frustum-shaped beam 150 produced by the transducer assembly 140 actuated by the single-channel amplifier circuit 1120, and shown in FIG. 11A, does not exhibit the spatial uniformity of the frustum-shaped beam 150 produced by the transducer assembly 140 actuated by the multi-channel amplifier circuit 230 via a frequency modulation scheme, and shown in FIG. 11B. Specifically, because the transducer assembly 140 in FIG. 11A is actuated by the single-channel amplifier circuit 1120, the transducer assembly 140 can be actuated at only one frequency at a given time point. The frustum-shaped beam 150 that is produced by the transducer assembly 140 being actuated by the single-channel amplifier circuit 1120 comprises a main lobe of energy and hot spots of energy.

Both the main lobe of energy and the hot spots of energy depicted in FIG. 11A exhibit increased energy intensity. However, because the hot spots are located in the near field and are not primarily located in the target treatment region 1110, this increase in intensity of the hot spots may cause tissue damage during treatment.

As discussed throughout this disclosure, the uniformity of the ultrasonic beam produced by the transducer assembly 140 is important for treatment. Spatial non-uniformity in the peak pressures in the near field can produce unwanted side effects, such as thermal tissue damage. Maximizing spatial uniformity in the peak pressures the far field can increase efficacy of treatment by enabling cavitation of synthetic cavitation nuclei within the region of insonation, thereby enabling fragmentation of pathological biomineralizations in proximity to the synthetic cavitation nuclei.

In some embodiments, to improve the spatial uniformity of the frustum-shaped beam 150, a multi-channel amplifier circuit can be used to enable frequency modulation. Frequency modulation refers to strategically altering the frequencies at which transducer elements operate over time, such that the pattern of constructive interference is changed. By changing the pattern of constructive interference, the pattern of energy concentration produced can also be changed to produce a more uniform spatial distribution of pressure over time.

In the embodiment depicted in FIG. 11B, the multi-channel amplifier circuit 230 comprises four channels such that the transducer assembly 140 can be actuated at four distinct frequencies at a given point in time. To generate the frustum-shaped beam 150 in FIG. 11B to exhibit peak pressures within the target treatment region 1110 that are within a prescribed range, a frequency modulation scheme can be employed. Frequency modulation is more efficient on the short axis because, for a rectangular aperture of an ultrasound transducer element, the solutions to the field in the Fresnel and Fraunhofer regimes are separable (where the Fresnel regime is a good approximation for the near field). Because the short axis produces sharper oscillations in pressure with respect to the z-axis due to the square dependence of the Fresnel regime on aperture radius, while the long axis produces more mild oscillations, to produce greater spatial uniformity in peak pressure distribution, a frequency modulation scheme should be implemented in the short axis. In some embodiments, such as the embodiment depicted in FIG. 11B, frequency modulation in the short axis can be implemented using elongated (e.g., an oblong shape with one dimension being larger than another dimension) ultrasound transducer elements arranged in a 1.5-dimensional array. The dimensions of the transducer assembly 140 can further be selected to be sufficiently large so as to not require precision alignment of the transducer assembly 140 during treatment.

FIG. 11B illustrates a frustum-shaped beam 150 produced as a result of a multi-channel amplifier circuit 230 modulating the frequencies of the transducer elements of the transducer assembly 140. The shape, size, position, and intensity of the frustum-shaped beam 150 depicted in FIG. 11B are a direct result of the pattern of constructive interference of the ultrasonic waves emitted from each of the plurality of transducer elements of the transducer assembly 140. In turn, this pattern of constructive interference is a direct result of the distinct frequencies at which the individual transducer elements operate. By modulating the frequencies at which the transducer elements operate, the pattern of constructive interference of acoustic energy, and thus the features of the frustum-shaped beam 150, can be changed.

In some embodiments, the frequencies of the plurality of states of the multi-channel amplifier circuit can include frequencies between 200 hertz and 2,000,000 hertz. In some embodiments, the frequencies of the plurality of states of the multi-channel amplifier circuit can have a center frequency of about 500,000 hertz.

The frustum-shaped beam 150 in FIG. 11B covers a greater volume within the target treatment region 1110 than the frustum-shaped beam of FIG. 11A. Specifically, unlike in FIG. 11A, the peak pressures of the frustum-shaped beam 150 within the target treatment region 1110 of FIG. 11B are within a prescribed range.

The frustum-shaped beam 150 of FIG. 11B also covers portions of the near field. However, the frustum-shaped beam 150 is more evenly distributed across the near field compared to the hot spots of FIG. 11A. As a result of this more even distribution, the intensity and pressure in the near field is diminished, thereby diminishing risk of injury to a patient undergoing treatment. In this way, frequency modulation of the transducer elements of the transducer assembly 140 enables a safer, and more efficacious treatment. To further prevent tissue damage, in some embodiments, a temperature of the ultrasound transducer assembly 140 does not surpass 43 degrees Celsius during production of the frustum-shaped beam 150.

Note that FIG. 11B is intended to illustrate only one embodiment of a method for increasing the uniformity of the spatial distribution of peak pressure. In alternative embodiments, alternative patterns of energy concentration produced by alternative sets of transducer elements operating at alternative sets of frequencies may be used to create a more uniform pressure distribution. In further embodiments, any quantity of distinct frequencies can be modulated to create a more uniform pressure distribution.

While frequency modulation of the transducer assembly 140 has many advantages for producing a spatially uniform pressure distribution, configuring the transducer assembly 140 for frequency modulation results in increased complexity of the transducer assembly 140, in part due to the increased quantity of transducer elements that comprise the transducer assembly 140 and are actuated to achieve the frequency modulation. More specifically, as frequencies of the transducer elements that comprise the transducer assembly 140 are modulated, electrical impendence also changes, which demands substantial changes in current. Therefore, as discussed in detail below with regard to FIG. 12, the transducer assembly 140 can be configured to include a small-enough quantity of transducer elements to ameliorate these changes in impedance during frequency modulation, but a large-enough quantity of transducer elements to optimize spatial uniformity of peak pressure distribution for the frustum-shaped beam 150.

Figure 12:
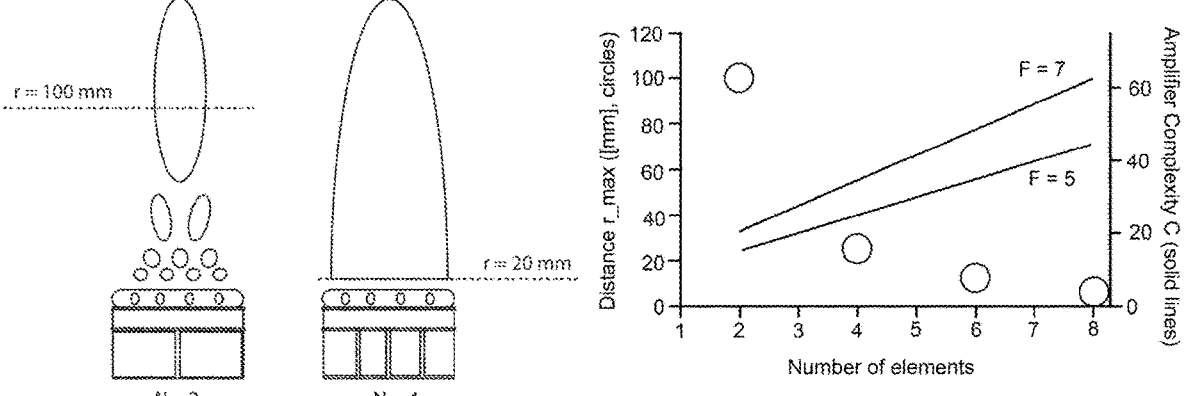
FIG. 12 is line graph that illustrates that phase shift, calculated for different quantities of transducer elements actuated at a given frequency modulation bandwidth ($\Delta F$), determines a closest point ($r_{min}$) in the target treatment region where the frequency modulation increases the uniformity of peak pressures in the target treatment region, in accordance with an embodiment.

FIG. 12 is line graph that illustrates that phase shift, calculated for different quantities of transducer elements actuated at a given frequency modulation bandwidth (ΔF), determines a closest point ($r_{min}$) in the target treatment region 1110 where the frequency modulation increases the uniformity of peak pressures in the target treatment region, in accordance with an embodiment.

As discussed throughout this disclosure, peak pressure distributions in the near field can be modified via frequency modulation. To understand the trade-offs between uniformity in peak pressure distribution produced via frequency modulation and complexity of multi-channel amplifier circuit configurations, a quantitative analysis of the closest point in the near field that can be modified by frequency modulation, was performed using a rectangular 1.5-dimensional ultrasound transducer assembly having a width of 13 wavelengths and performing frequency-modulated averaging along the short axis.

Specifically, Fresnel diffraction in the regime of the Fresnel number about equal to unity and near the axis of the ultrasound beam was examined. The advantage of looking at points along the beam axis is that the Fresnel diffraction criteria is met for small values of 0:

$$\frac{F\theta^2}{4} \ll 1 \tag{1}$$

For a planar, rectangular, ultrasonic, piston-like transducer assembly with dimensions in the x-y plane, the pressure at a point P was found using Huygens-Fresnel diffraction theory:

$$p = \frac{\sqrt{p_0}}{\sqrt{2}} e^{i\pi/4} \int_{u1}^{u2} e^{-i\pi u^2/2} du \int_{v1}^{v2} e^{-i\pi v^2/2} dv \tag{2}$$

where $u=x(2/\lambda r_0)^{1/2}$ and $v=y(2/\lambda r_0)^{1/2}$. The integrals along the spatial dimensions determine the relative amplitude of the pressure surface. To generate the entire pressure profile, the aperture was iteratively translated relative to point P and the pressure was calculated for each translation.

The Fresnel integrals (S and C) were used to express the spatial integral term:

$$\int_0^w e^{-i\pi w^2/2} dw = [S(w)+iC(w)] \tag{3}$$

The values of S and C are tabulated. The resulting phasor B=S+iC was used to display the maxima and minima as a function of the boundary conditions. Furthermore, since the integral is an odd function, the integral bridging the point zero was separated:

$$\int_{u1}^0 e^{-i\pi u^2/2} dw = [S(w)+iC(w)] \tag{4}$$

which restates that the resulting phasors from $u_1$ to 0 and 0 to $u_2$ are additive. We extend this to include when $u_1$ and $u_2$ are calculated using different wavelengths as expected for frequency modulation. For example:

$$u_1 = x_1(2/\lambda_1 r_0)^{1/2} \text{ and } u_2 = x_2(2/\lambda_2 r_0)^{1/2} \tag{5}$$

From the above analysis, it was determined that for w>1, frequency modulation can be beneficial in moving from a minima to a maxima or intermediate level simply by changing the frequency (and corresponding wavelength λ).

For extrema far from the surface of the transducer assembly but still in the near field, a ΔF of 100 kHz is sufficient for moving from a maxima to a minima. The phasor length is directly proportional to the width of the transducer elements (Equation 4), and therefore the ΔF in frequency modulation needed to average out the pressure distribution is inversely proportional to the square of the number of transducer elements. Therefore, as the number of transducer elements is increased, the ΔF in frequency modulation needed to achieve the same amount of averaging of the pressure field decreases. Using Equation 5, a general dependency relating the number of transducer elements, the frequency modulation, and the distance from the transducer assembly for producing a uniform pressure distribution was determined. First, a sufficient distance along the spiral of Cornu to produce averaging (e.g., Δu=2.7–2.4=0.3) was determined, and then this minimum change in phasor was expressed as follows in Equation 6:

$$\Delta u > x\left(\frac{2}{\lambda_1 r} - \frac{2}{\lambda_2 r}\right)^{1/2} \tag{6}$$

where $$r = \frac{2x^2(\Delta f)}{cu_{min}^2} \tag{7}$$

From this, the pitch of the transducer elements (2x, assuming the point P is symmetrically centered with respect to the transducer element) for a given frequency modulation ΔF or Δλ) to the distance r from the transducer assembly was determined. Varying the number of transducer elements, the number of transducer elements needed to achieve a uniform distribution increases as the distance r decreases towards the surface of the transducer assembly. This conclusion is illustrated in the line graph in FIG. 12.

Although $r_{min}$ decreases with increasing number of transducer elements (decreasing pitch), the complexity of the multi-channel amplifier circuit, C, increases with increasing number of transducer elements (for a frequency modulation scheme using 5 or 7 discrete frequencies).

For clinical use, maximum acoustic power levels set forth in established diagnostic ultrasound standards can be taken as levels that can safely be delivered. Electrical amplifier circuits capable of greater than 1 kW peak power are typically limited by thermal considerations, and therefore can either not match these levels of peak power for sufficient periods of time, or rely upon thermally efficient designs.

One class of amplifier circuit that can reach sufficient thermal efficiency for high peak power requirements is the class D amplifier circuit. However, class D amplifier circuits use a multiplexer to connect each channel to each frequency, which results in complexity during frequency modulation. Given N channels and F discrete frequencies, the actuating circuit complexity, C, can be modeled as:

$$C=N \times F \tag{8}$$

Furthermore, to achieve sufficiently high pulse repetition frequencies, the circuit contains separate power sources for each frequency:

$$C=F+(N \times F) \tag{9}$$

In this metric, C represents a complexity which correlates with the approximate footprint for a circuit. For example, for N=4 and F=7, the power sources and the multiplexer account for about 70% of the circuit board area. Therefore, the complexity increases with both the number of channels and the number of frequencies used in the frequency modulation scheme.

Figure 13:
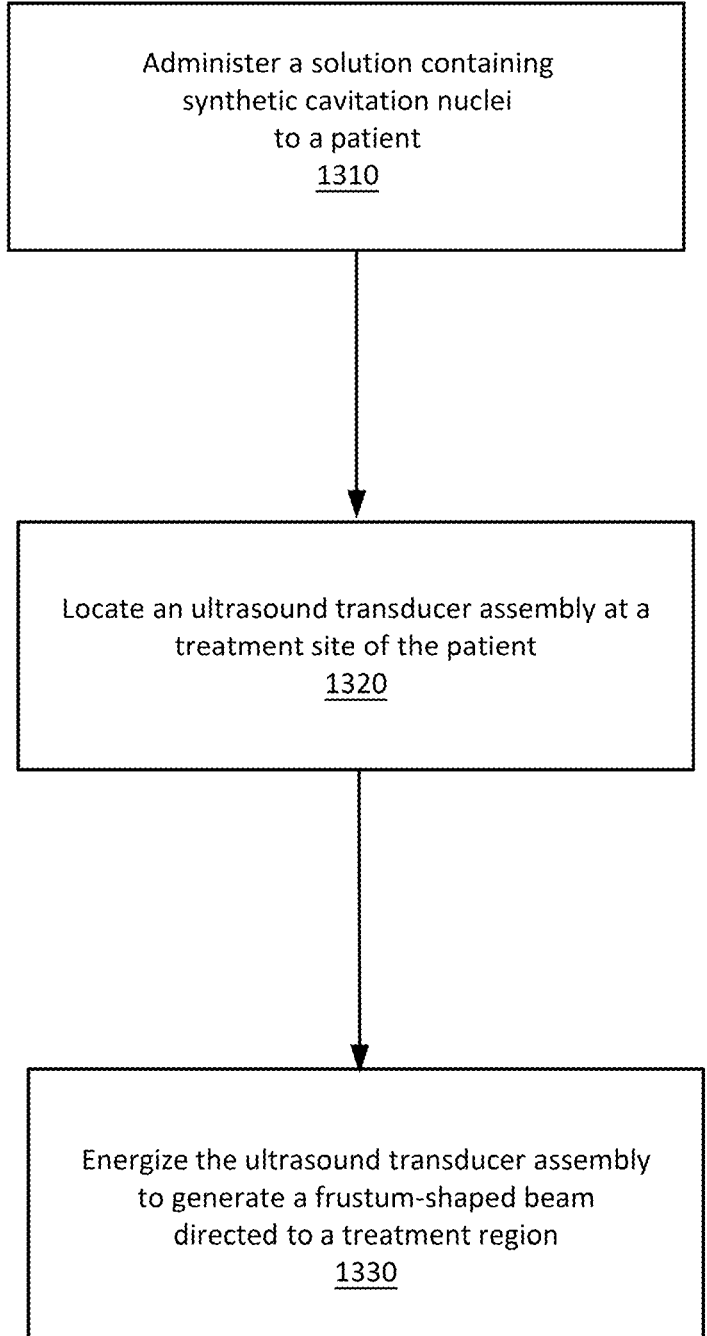
FIG. 13 is a flow chart of a method for fragmenting one or more biomineralizations located in a vessel of a patient, in accordance with an embodiment.

Based on this parameter study, there is a trade-off between the minimum distance from the transducer assembly surface that that spatial distribution of peak pressures can be modified by a given ΔF during frequency modulation, and the complexity of the amplifier circuit. Based on this, a transducer assembly configuration that incorporates a number of transducer elements between 4 and 8 is sufficient for implementation of a frequency modulation scheme that optimizes the joint constraints of achieving sufficient uniformity of peak pressure and minimizing amplifier circuit complexity. Methods FIG. 13 is a flow chart of a method for fragmenting one or more biomineralizations located in a vessel of a patient, in accordance with an embodiment. In other embodiments, the method may include different and/or additional steps than those shown in FIG. 13. Additionally, steps of the method may be performed in different orders than the order described in conjunction with FIG. 13 in various embodiments.

A care provider administers 1310 a solution containing synthetic cavitation nuclei to the patient. The patient to which the solution containing synthetic cavitation nuclei is administered 1310 contains at least one biomineralization within the patient's vessel. The care provider may be any unit capable of providing care. In some embodiments, the care provider may be a physician or a nurse. In alternative embodiments, the care provider may be a machine, device, or apparatus.

The solution containing synthetic cavitation nuclei may be administered 1310 to the patient in a variety of ways. In some embodiments, the solution is introduced directly at the target treatment region, such as by direct implantation into a target tissue or mass. In other embodiments, the solution is introduced at a remote location (e.g., into the bloodstream via percutaneous injection) and the synthetic cavitation nuclei can travel to, and concentrate at, the treatment region. Delivery of the solution containing synthetic cavitation nuclei is discussed in greater detail above with regard to FIG. 1. In some embodiments, step 1310 is optional.

The care provider locates 1320 an ultrasound assembly at a treatment site of the patient. In some embodiments, the ultrasound assembly is the ultrasound assembly 140 described with regard to FIGS. 1-7. In some embodiments, the treatment site comprises a portion of the patient's skin. In certain embodiments, the treatment site may be determined without the use of real-time imaging. However in some embodiments the treatment site may be determined using guidance from one or more pre-operative diagnostic tools and/or bony landmarks of the patient.

The ultrasound assembly is located 1320 at the treatment site such that actuation of the ultrasound transducer assembly by a multi-channel amplifier circuit as discussed above, causes the ultrasound transducer assembly to insonate a treatment region described with regard to step 1330 below. In embodiments in which the patient's vessel is a ureter, and the treatment region comprises an upper half of the ureter, locating 1320 the ultrasound transducer assembly at the treatment site comprises placing the ultrasound transducer assembly, and in some embodiments a standoff pad of the ultrasound transducer assembly, in contact with skin located on a posterior face of the patient's body. In alternative embodiments in which the patient's vessel is a ureter, and the treatment region comprises a lower half of the ureter, locating 1320 the ultrasound transducer assembly at the treatment site comprises placing the ultrasound transducer assembly, and in some embodiments a standoff pad of the ultrasound transducer assembly, in contact with skin located on an anterior face of the patient's body. In some further embodiments, the ultrasound transducer assembly may further be placed in contact with a buffer material such as an ultrasound gel, that is in contact with the patient's skin.

The care provider energizes 1330 the ultrasound transducer assembly to generate a frustum-shaped beam directed to a treatment region. In some embodiments, the frustum-shaped beam is the frustum-shaped beam described with regard to FIGS. 1-7. In some embodiments, the treatment region may be an area of the patient's body located within a certain proximity of the treatment site. For example, the treatment region may comprise a section of the patient's ureter as described above.

In certain embodiments, the insonation is effective to cause cavitation of synthetic cavitation nuclei administered in step 1310. And in further embodiments, cavitation of the synthetic cavitation nuclei releases sufficient energy to cause fragmentation of the at least one biomineralization located in the patient's vessel.

Figure 14:
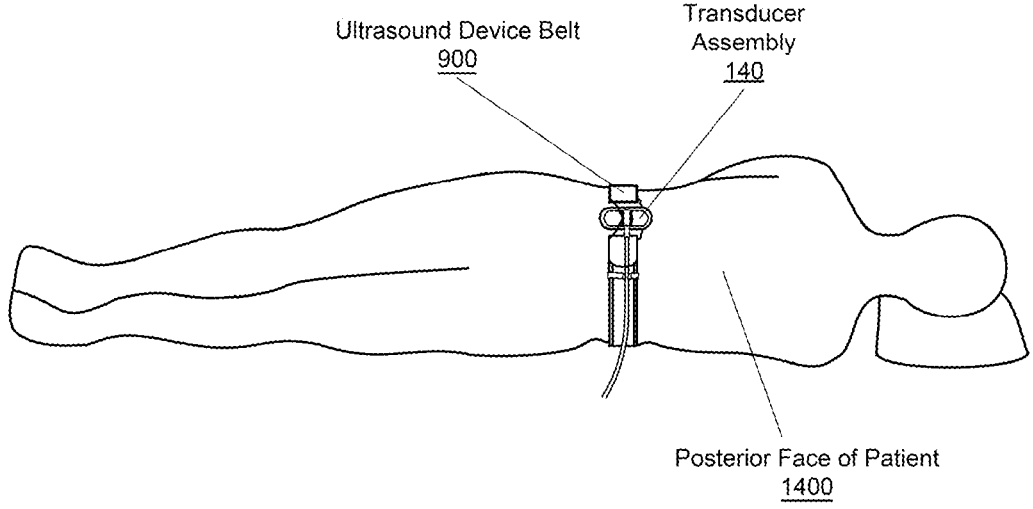
FIG. 14 illustrates use of the ultrasound device belt of FIG. 9, in accordance with an embodiment.

FIG. 14 illustrates use of the ultrasound device belt 900 described with regard to FIG. 9, in accordance with an embodiment. Specifically, the transducer assembly 140 is attached to the ultrasound device belt 900, and secured to a posterior face of the patient's body 1400 by the ultrasound device belt 900. In this configuration, the patient receives insonation via the transducer assembly 140.

As described above with regard to FIG. 13, the ultrasound assembly 140 is positioned with respect to the patient's body such that the ultrasound assembly is able to insonate a desired area of the body called the "treatment region." In embodiments in which the treatment region comprises an upper half of the ureter, the ultrasound device belt 900 is positioned such that the ultrasound transducer assembly 140 is placed in contact with skin located on the posterior face of the patient's body 1400, as shown in FIG. 14. In alternative embodiments in which the treatment region comprises a lower half of the ureter the ultrasound device belt 900 is positioned such that the ultrasound transducer assembly 140 is placed in contact with skin located on an anterior face of the patient's body (not shown).

In some embodiments, the transducer assembly 140 is placed in uniform contact with the skin of the patient. In some further embodiments, the ultrasound device belt 900 is positioned to secure the ultrasound transducer assembly 140 at an angle relative to a plane of the skin of the patient's body. In additional embodiments, a buffer material is placed between the ultrasound assembly 140 and the skin of the patient. The buffer material may be any type of material including an ultrasound gel.

EXAMPLES

Figure 15A:
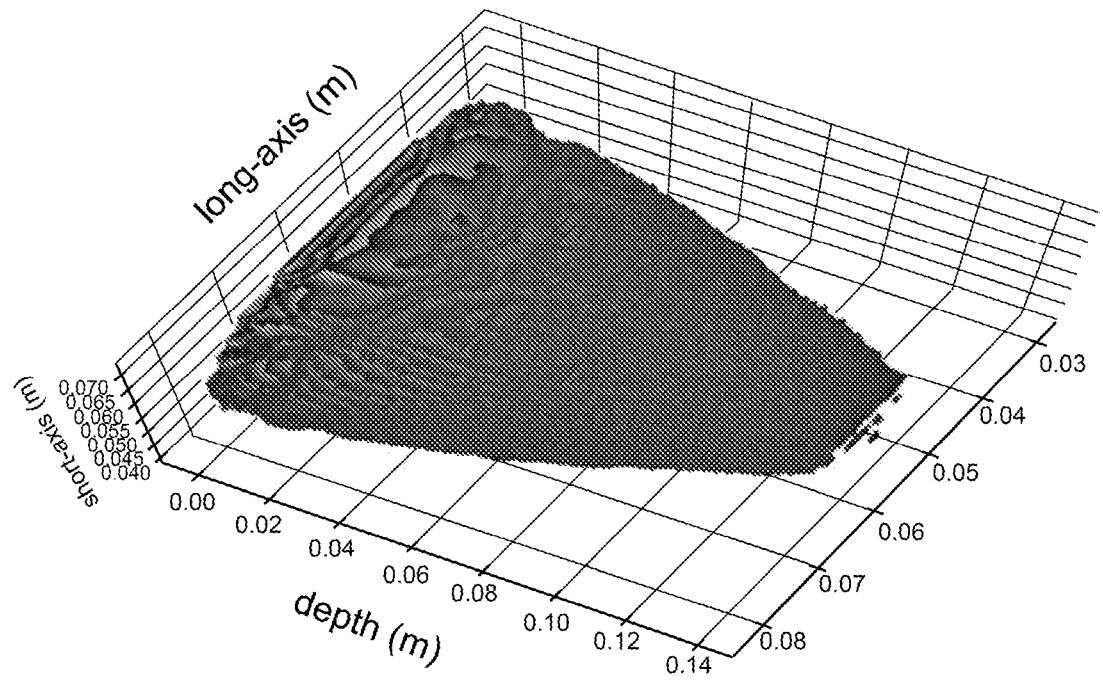
FIG. 15A is a first view of a simulation of a frustum-shaped beam produced using the ultrasound transducer assembly shown in FIG. 5, in accordance with an embodiment.

FIG. 15A is a first view of a simulation of a frustum-shaped beam produced using the ultrasound transducer assembly shown in FIG. 5, in accordance with an embodiment. The simulation was generated using finite element analysis. Specifically, the simulation shown in FIG. 15A was generated using a computer-simulation program. The computer-simulation program that was used was the PZFlex simulation program distributed by Weidlinger Associates, located in Mountain View, California. The specific PZFlex simulation program used to generate the simulation corresponds to PZFlex version 2017. However, in alternative embodiments, any alternative computer-simulation program can be used to simulate the frustum-shaped beam as described herein.

Entry of operating variables of the transducer assembly as inputs into the PZFlex simulation program enabled generation of the simulation. In other words, an embodiment of the transducer assembly was simulated by the PZFlex simulation program to generate the simulation. The embodiment of the transducer assembly that was used to generate the simulation shown in FIG. 15A comprised a first dimension of 3.6 cm and a second dimension of 7.2 cm. Furthermore, the embodiment of the transducer assembly that was used to generate the simulation comprised a total of 8 transducer elements, including 4 transducer elements located in a center of the transducer assembly and 4 transducer elements located peripherally in the transducer assembly.

The 8 transducer elements in the embodiment of the transducer assembly that was used to generate the simulation were simulated as frequency modulated pressure sources. The frequency modulation scheme used by the transducer elements to generate the simulation is shown below in Table 1. As depicted in Table 1, the frequency modulation scheme used by the transducer elements to generate the simulation comprised 12 bursts of frequencies (e.g., Burst 1, Burst 2, Burst 3, etc.). Each burst occurred over a unique range in time. Specifically, each burst was generated for a minimum of 33 microseconds before the next burst was initiated. The bursts also occurred in chronological order. In other words, Burst 1 occurred, then Burst 2 occurred, a subsequent Burst 3 occurred, and so on.

As shown in Table 1, each burst of frequency comprised four frequencies (Frequency 1, Frequency 2, Frequency 3, and Frequency 4). Each frequency of the four frequencies that comprised a burst was actuated on 2 of the transducer elements. Specifically, each frequency was actuated on 1 transducer element located in the center of the transducer assembly and 1 transducer element located peripherally in the transducer assembly. Each center transducer element was assigned the same relative amplitude, while each peripheral transducer element generated a pressure equivalent to half of the pressure generated by the center transducer elements. This difference between the center transducer elements and the peripheral transducer elements was established in an effort to model electrical apodization of the peripheral transducer elements.

TABLE 1

| | Frequency 1 (kHz) | Frequency 2 (kHz) | Frequency 3 (kHz) | Frequency 4 (kHz) |
|---|---|---|---|---|
| Burst 1 | 466 | 533 | 500 | 566 |
| Burst 2 | 433 | 566 | 466 | 600 |
| Burst 3 | 400 | 600 | 433 | 566 |
| Burst 4 | 500 | 566 | 466 | 533 |
| Burst 5 | 466 | 533 | 433 | 500 |
| Burst 6 | 433 | 500 | 400 | 466 |
| Burst 7 | 533 | 466 | 500 | 433 |
| Burst 8 | 566 | 433 | 533 | 400 |
| Burst 9 | 600 | 400 | 566 | 433 |
| Burst 10 | 500 | 433 | 533 | 466 |
| Burst 11 | 533 | 466 | 566 | 500 |
| Burst 12 | 566 | 500 | 600 | 533 |

To generate the simulation, the frequency modulation scheme depicted in Table 1 was run as described above in a volume comprising a first dimension of 11.2 cm, a second dimension comprising 11.2 cm, and a third dimension comprising 20 cm. The periphery of the volume comprised perfectly absorbing layers. The frequency modulation scheme was run until the simulation reached a steady state throughout the entire volume.

Subsequently, each burst of frequency was sampled over 33 microseconds, and the total distribution of the simulation was calculated from the pressure values for all 12 frequency bursts. The result, shown in FIG. 15A, is a −6 dB isobaric volume distribution. In other words, as shown in FIG. 15A, the simulation has a spatially uniform peak pressure distribution within the volume in which the simulation was generated. In a preferred embodiment, a local peak pressure within the volume was between 6 MPa and 0.1 MPa. Furthermore, a local minimum peak pressure of the simulated beam was within about 50% (+/−25%) of a local maximum peak pressure of the simulated beam. In other words, pressure was maintained with about 50% (+/−25%) uniformity over the entire volume of the simulated beam.

The simulation was validated by comparing additional simulations generated using the PZFlex simulation program to analytical solutions generated using the Fresnel formulation for diffraction. The additional simulations were run as a function of number of grid points per wavelength, from $8\delta$ to 17, and the additional simulations were compared to the analytical solution for cross-sections of the long and short axis. The goodness of fit was ascertained using a r-squared statistic, and a grid spacing of 15 points per wavelength was found to have sufficient accuracy ($r^2=0.99$) across the Fresnel regime.

Figure 15B:
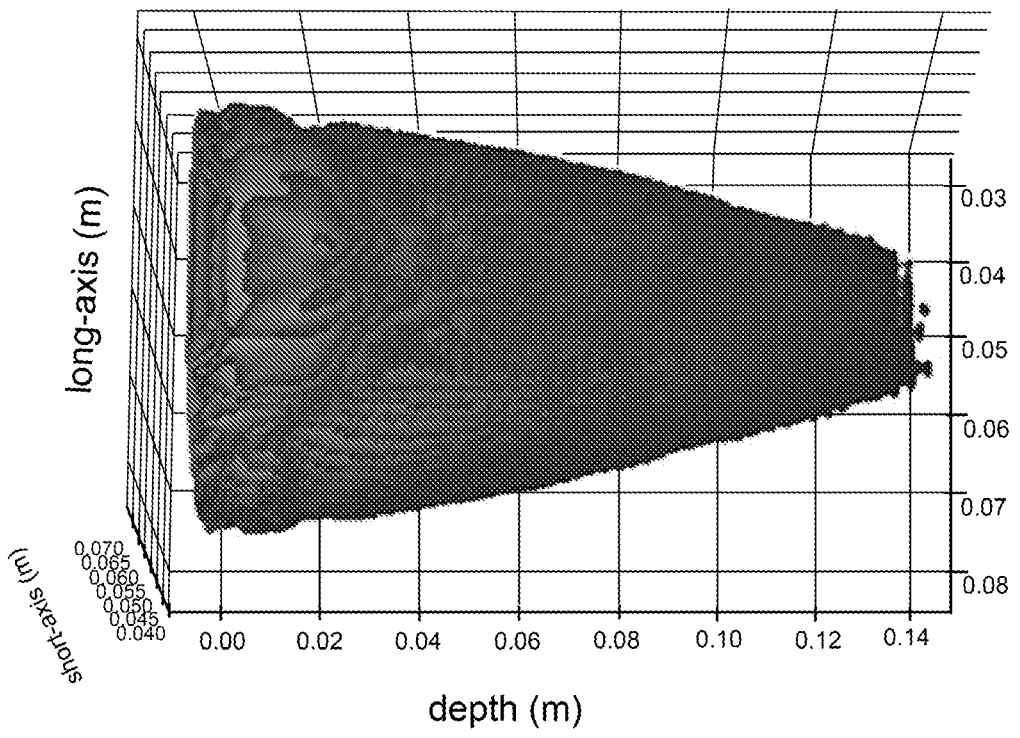
FIG. 15B is a second view of the simulation the frustum-shaped beam shown in FIG. 15A, in accordance with an embodiment.

FIG. 15B is a second view of the simulation of the frustum-shaped beam shown in FIG. 15A, in accordance with an embodiment. The method by which the simulation shown in FIG. 15B was generated is described above with regard to FIG. 15A.

Figure 15C:
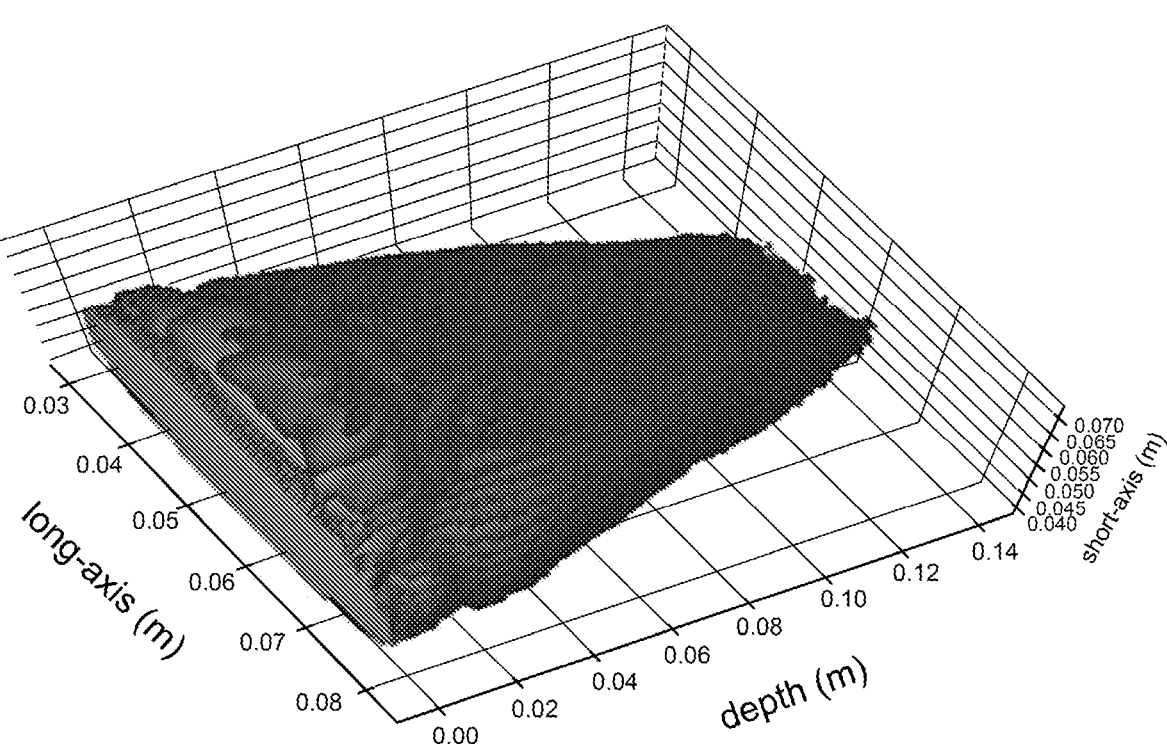
FIG. 15C is a third view of the simulation the frustum-shaped beam shown in FIGS. 15A and 15B, in accordance with an embodiment.

FIG. 15C is a third view of the simulation of the frustum-shaped beam shown in FIGS. 15A and 15B, in accordance with an embodiment. The method by which the simulation shown in FIG. 15C was generated is described above with regard to FIG. 15A.

Figure 16A:
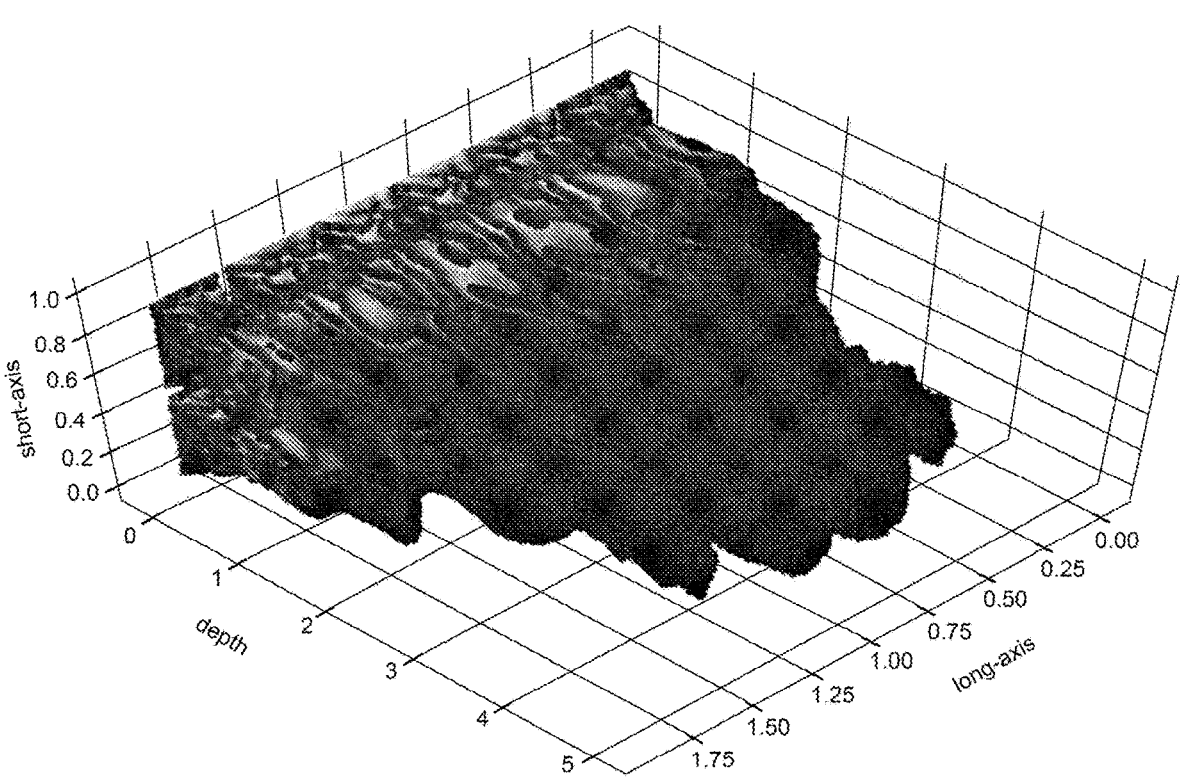
FIG. 16A is a first view of a simulation of a frustum-shaped beam produced using the ultrasound transducer assembly shown in FIG. 8, in accordance with an embodiment.

FIG. 16A is a first view of a simulation of a frustum-shaped beam produced using the ultrasound transducer assembly 800 shown in FIG. 8, in accordance with an embodiment. The simulation was generated according to a method similar to the method described above with regard to FIG. 15A.

As discussed above, the ultrasound transducer assembly 800 comprises 3 groups 810A-C of four ultrasound transducer elements. One group of the transducer elements (group 810B) is a center group of transducer elements. The other two groups of the transducer elements (groups 810A and 810C) are peripheral groups of transducer elements.

The transducer elements were simulated as frequency modulated pressure sources. The frequency modulation scheme used by the transducer elements to generate the simulation is shown below in Table 2. As depicted in Table 2, the frequency modulation scheme used by the transducer elements to generate the simulation comprised 8 bursts of frequencies. Each frequency of the four frequencies that comprised a burst was actuated on each of 4 channels. Each burst occurred over a unique range in time. Each burst occurred over a unique range in time. Specifically, each burst was generated for a minimum of 33 microseconds before the next burst was initiated. The bursts also occurred in chronological order.

As shown in Table 1, each burst of frequency comprised four frequencies (Frequency 1, Frequency 2, Frequency 3, and Frequency 4). Each center transducer element (e.g., transducer elements associated with the group 810B) was assigned the same relative amplitude, while the peripheral transducer elements (e.g., transducer elements associated with the groups 810A and 810C) were actuated at a pressure of either 0.7 or 0.85 of the center transducer elements, to model the electrical apodization of peripheral transducer elements. Specifically, transducer elements 1a, 4a, 2c, and 4c were actuated at a pressure of 0.7 of the center transducer elements, and transducer elements 2a, 3a, 1c, and 3c were actuated at a pressure of 0.85 of the center transducer elements.

TABLE 2

|  | Frequency 1 (kHz) | Frequency 2 (kHz) | Frequency 3 (kHz) | Frequency 4 (kHz) |
|---|---|---|---|---|
| Burst 1 | 563.5 | 629.5 | 596.5 | 530.5 |
| Burst 2 | 530.5 | 563.5 | 629.5 | 596.5 |
| Burst 3 | 596.5 | 530.5 | 563.5 | 629.5 |
| Burst 4 | 629.5 | 596.5 | 530.5 | 563.5 |
| Burst 5 | 596.5 | 629.5 | 563.5 | 530.5 |
| Burst 6 | 530.5 | 596.5 | 629.5 | 563.5 |
| Burst 7 | 563.5 | 530.5 | 596.5 | 629.5 |
| Burst 8 | 629.5 | 563.5 | 530.5 | 596.5 |

To generate the simulation, the frequency modulation scheme depicted in Table 2 was run in a volume comprising a first dimension of 8 cm, a second dimension comprising 5 cm, and a third dimension comprising 25 cm. The periphery of the volume comprised perfectly absorbing layers. The frequency modulation scheme was run until the simulation reached a steady state throughout the entire volume.

Subsequently, each burst of frequency was sampled over 33 microseconds, and the total distribution of the simulation was calculated from the average pressure values for all 8 frequency bursts. The result, shown in FIG. 16A, is a −8 dB isobaric volume distribution.

Figure 16B:
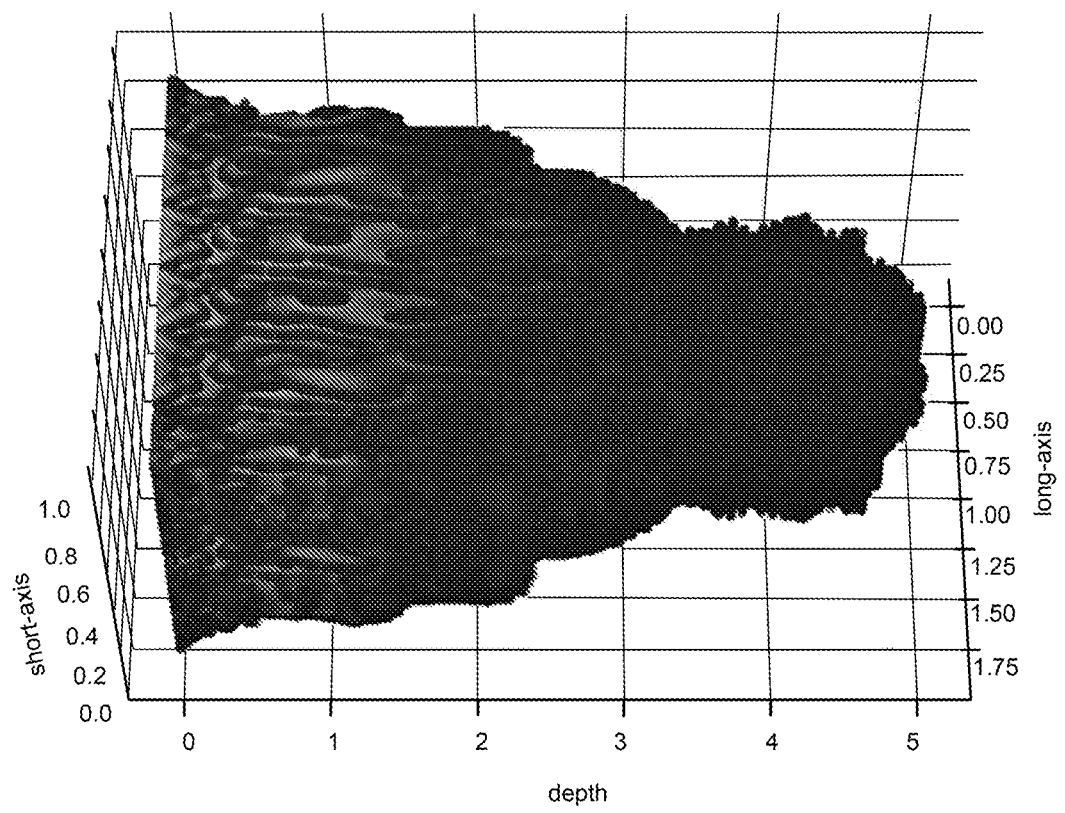
FIG. 16B is a second view of the simulation the frustum-shaped beam shown in FIG. 16A, in accordance with an embodiment.

FIG. 16B is a second view of the simulation of the frustum-shaped beam shown in FIG. 16A, in accordance with an embodiment. The method by which the simulation shown in FIG. 16B was generated is described above with regard to FIG. 16A.

Figure 16C:
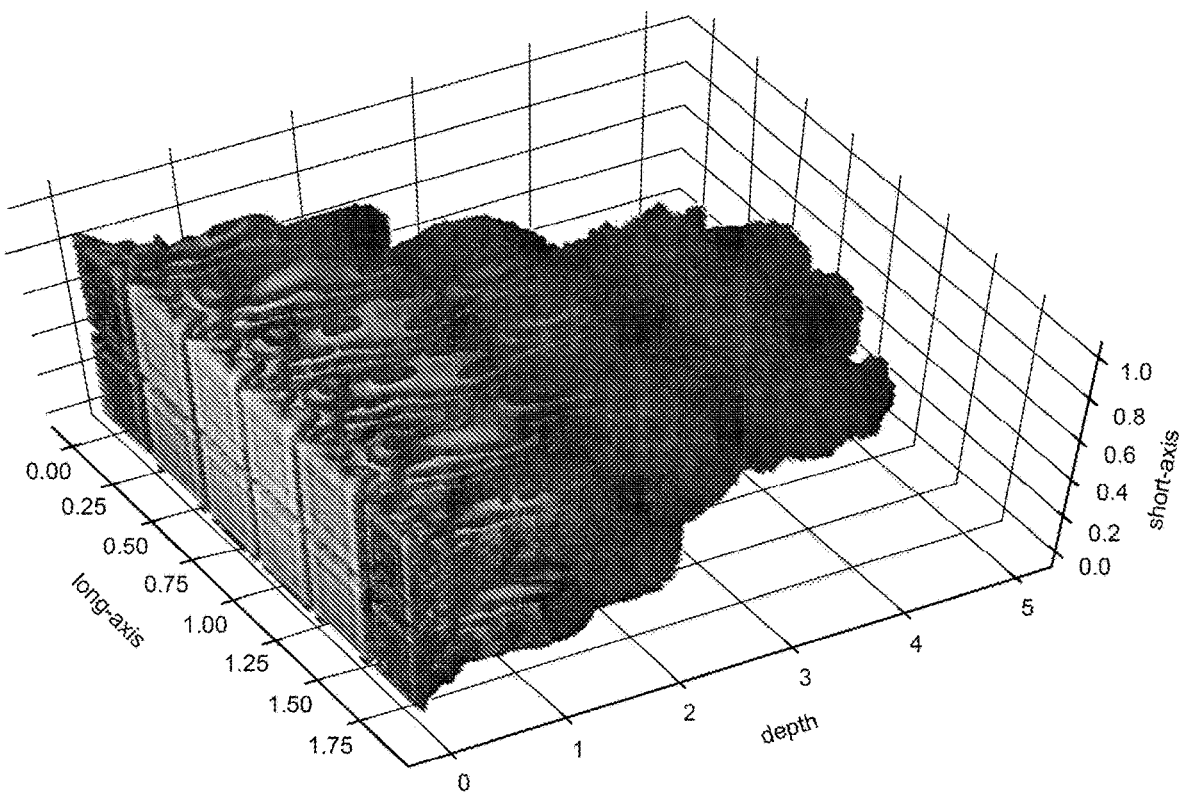
FIG. 16C is a third view of the simulation the frustum-shaped beam shown in FIGS. 16A and 16B, in accordance with an embodiment.

FIG. 16C is a third view of the simulation of the frustum-shaped beam shown in FIGS. 16A and 16B, in accordance with an embodiment. The method by which the simulation shown in FIG. 16C was generated is described above with regard to FIG. 16A.

Figure 17:
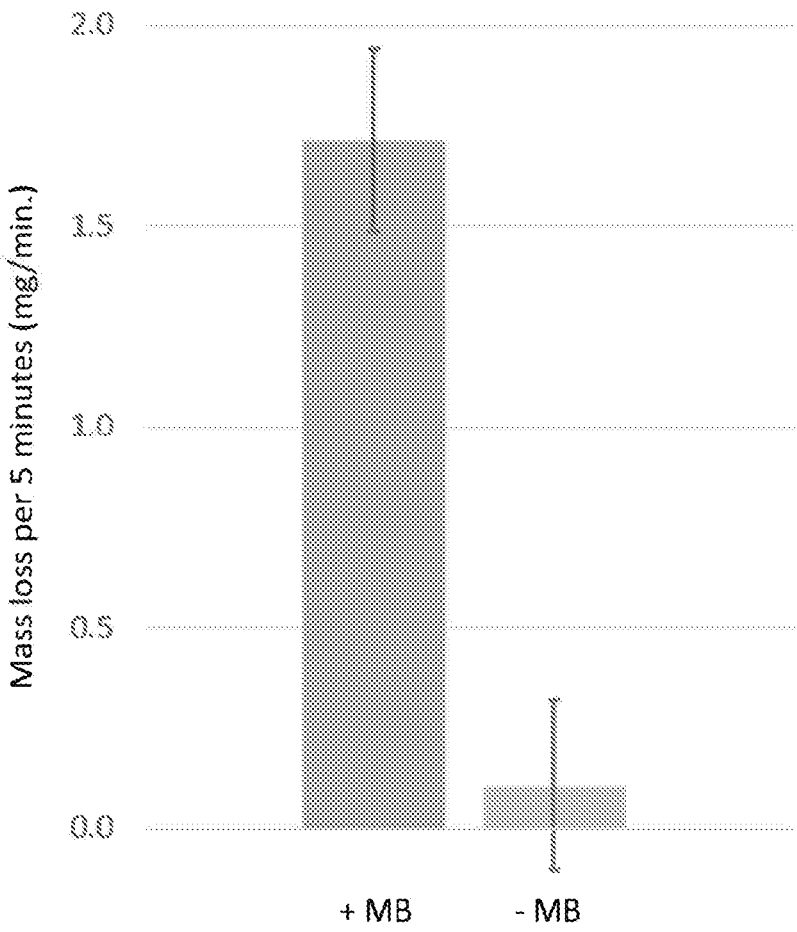
FIG. 17 is a bar graph depicting the mass of a synthetic urinary stone throughout the duration of treatment using synthetic cavitation nuclei and an ultrasound device according to the embodiments disclosed herein.

FIG. 17 is a bar graph depicting a loss of mass of a synthetic urinary stone throughout the duration of treatment using synthetic cavitation nuclei and an ultrasound device according to the embodiments disclosed herein. To generate the data included in FIG. 17, synthetic cavitation nuclei were placed in proximity to a synthetic urinary stone (hydroxy-apatite-Ca-microcrystalline cellulose, Riogen Corp.) and insonated with a transducer device in accordance with the embodiments described herein.

The transducer device included 4 transducer elements. To perform the insonation, the transducer device was positioned 10 cm from the urinary stone. Treatment was produced iteratively, with 10 seconds of synthetic cavitation nuclei placement followed by 10 seconds of insonation. Insonation was achieved with an exemplary device, where the transducer elements of the device were actuated with a center frequency of 500 kHz at a frequency modulation scheme comprising 34 kHz frequency steps (e.g., a frequency modulation scheme including frequencies of 549.5 kHz, 516.5 kHz, 483.5 kHz, and 450.5 kHz), 100 Hz pulse repetition frequency, and peak negative pressure of 1.2 MPa as verified by hydrophone (Onda Corp.).

The mass of the synthetic urinary stone was measured every 5 minutes for a total of 45 minutes of treatment time. The measured loss of mass of the synthetic urinary stone is depicted in FIG. 17, and is compared with loss of mass of a control synthetic urinary stone via erosion in the absence of synthetic cavitation nuclei. As shown in FIG. 17, the loss of mass experienced by the synthetic urinary stone that underwent the experimental treatment is significant relative to the loss of mass of the control synthetic urinary stone.

FIG. 18A is an image depicting a Calcein fluorescence-labeled aortic valve before treatment using synthetic cavitation nuclei and an ultrasound device according to the embodiments disclosed herein. FIG. 18B is an image depicting a Calcein fluorescence-labeled aortic value after treatment using synthetic cavitation nuclei and an ultrasound device according to the embodiments disclosed herein. As shown in FIG. 18B, there is a reduced amount of calcium present in the aortic valve after treatment, compared to before treatment. FIG. 18C is a graph depicting an intensity transverse profile of the Calcein fluorescence-labeled aortic value before treatment and an intensity transverse profile of the Calcein fluorescence-labeled aortic value after treatment, normalized to the maximum intensity of the before sample, with background fluorescence subtracted.

To generate the data included in FIGS. 18A-C, an aortic heart valve (AHV) was extracted from bovine heart (Prather Ranch) and placed in a mechanical agitator at 300 rpm with calcium phosphate solution ([Ca] at 13 mg/dL and [$PO_4$] at 10 mg/dL with the final solution adjusted to pH 7.4) according to Pettenazzo et al. protocol (available on the world wide web at URL www.ncbi.nlm.nih.gov/pubmed/11241085), after pre-treatment with glutaraldehyde. After >45 days the AHV was removed and washed with buffered saline (0.9%) and placed in 10 μM Calcein (Fluka) solution in dulbecco PBS, at room temperature, overnight. The sample was then washed three times with buffered saline (0.9%). The fluorescence was observed on a Leica microscope and Leica camera using fluorescence (ex. 470/40 nm, em. 525/50 nm, 4× objective). The before treatment image of the Calcein fluorescence-labeled aortic valve is depicted in FIG. 18A.

The AHV was then incubated in 1 mM $MgSO_4$ overnight to remove Calcein for treatment. The AHV was placed in a solution of dPBS before treatment. The treatment set-up was as follows: Synthetic cavitation nuclei were placed in proximity to the AHV and insonated with a transducer device in accordance with the embodiments described herein. To place synthetic caviation nuclei, 1 mL of synthetic cavitation nuclei configured to complex with calcium-containing biomineralizations and having a mean diameter of 1.243 μm and a number density of $1.6×10^8$/mL were placed in proximity to the AHV. The transducer device used for insonation included 4 transducer elements. To perform the insonation, the AHV was mounted in a dialysis tubing and placed 10 cm from the surface of the ultrasound transducer in buffered saline with atmospheric concentrations of dissolved gas.

During insonation with an exemplary device, the transducer elements of the device were actuated with a center frequency of 500 kHz at a frequency modulation scheme comprising 34 kHz frequency steps (e.g., a frequency modulation scheme including frequencies of 549.5 kHz, 516.5 kHz, 483.5 kHz, and 450.5 kHz), 100 Hz pulse repetition frequency with 5% duty cycle, and peak negative pressure corresponding to a mechanical index of 1.9 as verified by a Y107 hydrophone (Sonic Concepts).

Treatment proceeded iteratively, with of 30 iterations of synthetic cavitation nuclei solution placement and insonation. Each iteration consisted of 30 seconds of synthetic cavitation nuclei incubation and injection, followed by 30 seconds of treatment time. After 30 iterations, the AHV was placed in 30 μM Calcein in dPBS and allowed to incubate overnight. The AHV was rinsed with buffered saline twice, then imaged using fluorescence (excitation 470/40 nm, emission 525/50 nm, 4× objective). The after treatment image of the Calcein fluorescence-labeled aortic valve is depicted in FIG. 18B.

The gain on the camera was equal in the captured images of the Calcein fluorescence-labeled aortic valve both pre-treatment and post-treatment, thereby allowing for direct comparison. The green channel from each image was analyzed using ImageJ. FIG. 18C is a graph depicting an intensity transverse profile of the Calcein fluorescence-labeled aortic value before treatment and an intensity transverse profile of the Calcein fluorescence-labeled aortic value after treatment, normalized to the maximum intensity of the before sample, with background fluorescence subtracted. The maximum intensity of the pre-treatment image is 170.05+/−1.08 AU and the maximum intensity of the post-treatment image is 139.6+/1 AU. The background was found to be about 115 AU for both images, consistent with equivalent non-specific binding of Calcein between the two images. Decreased calcification was observed in the post-treatment image, as represented by the central plateau (about 40% lower) in the fluorescent profile intensities depicted in FIG. 18C.

We claim:

1. An ultrasound device comprising:
an ultrasound transducer assembly comprising:
a plurality of ultrasound transducer elements arranged in an array and contained within an external housing; and
a multi-channel amplifier circuit, wherein each channel of the multi-channel amplifier circuit is configured to actuate a distinct subset of the plurality of ultrasound transducer elements,
wherein the multi-channel amplifier circuit is configured to operate in each of a plurality of states, each state of the plurality of states comprising a set of frequencies, each set of frequencies comprising a frequency at which each channel of the multichannel amplifier circuit is configured to actuate the distinct subset of the plurality of ultrasound transducer elements, and
wherein the multi-channel amplifier circuit is configured to switch between the plurality of states, thereby causing the plurality of ultrasound transducer elements to produce a frustum-shaped beam,
wherein the frustum-shaped beam comprises a plurality of longitudinal acoustic waves, each longitudinal acoustic wave of the plurality of longitudinal acoustic waves produced by one of the plurality of ultrasound transducer elements, and constructive and destructive interference of the longitudinal acoustic waves yields approximately uniform peak pressures throughout a frustum-shaped volume, and wherein the peak pressures are within 50% of a global maximum peak pressure within the volume.

2. The ultrasound device of claim 1, wherein the frustum-shaped beam comprises a plurality of longitudinal acoustic waves, each longitudinal acoustic wave of the plurality of longitudinal acoustic waves produced by one of the plurality of ultrasound transducer elements, and wherein peak pressures of the frustum-shaped beam are between 0.5 megapascals and 10 megapascals when measured in water.

3. The ultrasound device of any one of claims 1-2, wherein the frustum-shaped beam comprises a first frustum base, a second frustum base, and a first distance between the first frustum base and the second frustum base,
wherein the first frustum base is located a second distance from a surface of the ultrasound transducer assembly from which the plurality of ultrasound transducer elements produce the frustum-shaped beam,
wherein the first frustum base and the second frustum base are parallel to the surface of the ultrasound transducer assembly, and
wherein the first distance is at least 12 cm.

4. The ultrasound device of claim 3, wherein an area of the first frustum base is larger than an area of the second frustum base.

5. The ultrasound device of claim 3, wherein the second distance is about 2 cm.

6. The ultrasound device of any one of claims 1-2, wherein the plurality of ultrasound transducer elements comprises piezoelectric transducers.

7. The ultrasound device of any one of claims 1-2, wherein the plurality of ultrasound transducer elements comprises capacitive micromachined elements.

8. The ultrasound device of any one of claims 1-2, wherein one or more of the plurality of ultrasound transducer elements are apodized.

9. The ultrasound device of any one of claims 1-2, wherein the plurality of ultrasound transducer elements comprises at least 4 ultrasound transducer elements and at most 8 ultrasound transducer elements.

10. The ultrasound device of any one of claims 1-2, wherein the plurality of ultrasound transducer elements comprises 4 ultrasound transducer elements.

11. The ultrasound device of any one of claims 1-2, further comprising two transistors associated with each channel of the multi-channel amplifier circuit, wherein the two transistors are configured to control the frequency at which the channel actuates the distinct subset of the plurality of ultrasound transducer elements based on the state of the multichannel amplifier circuit, and wherein the two transistors are configured to operate in an alternating manner, thereby causing the distinct subset of the plurality of ultrasound transducer elements to produce an acoustic wave at a frequency between 100 kHz and 10,000 kHz based on the state of the multi-channel amplifier circuit.

12. The ultrasound device of claim 11, further comprising an electrical filter associated with each channel of the multi-channel amplifier circuit, wherein the electrical filter is configured to filter out high frequency components from the acoustic wave.

13. The ultrasound device of any one of claims 1-2, wherein the multi-channel amplifier circuit further comprises at least one power source that is configured to supply a constant voltage throughout a duration of a state of the multi-channel amplifier circuit.

14. The ultrasound device of claim 13, wherein the at least one power source further comprises at least two power sources, and wherein each of the at least two power sources is configured to supply a distinct constant voltage throughout a duration of a state of the multichannel amplifier circuit, and wherein the multi-channel amplifier circuit further comprises:
two transistors associated with each channel of the multi-channel amplifier circuit, wherein the two transistors are configured to control the frequency at which the channel actuates the distinct subset of the plurality of ultrasound transducer elements based on the state of the multi-channel amplifier circuit, and wherein the two transistors are configured to operate in an alternating manner, thereby causing the distinct subset of the plurality of ultrasound transducer elements to produce a pressure wave at a frequency between 100 kHz and 10,000 kHz based on the state of the multichannel amplifier circuit; and at least one multiplexer, each multiplexer of the at least one multiplexer configured to connect one or more of the at least two power sources to the two transistors associated with each channel of the multi-channel amplifier circuit.

15. The ultrasound device of claim 14, wherein each of the at least two power sources comprises a capacitor that is configured to charge at a charging rate such that the capacitor reaches a desired voltage during a period of time that is less than a duration of an off-state of the multi-channel amplifier circuit, the off-state of the multi-channel amplifier circuit defined by each channel of the multi-channel amplifier circuit actuating the subsets of ultrasound transducer elements at a frequency of 0 hertz.

16. The ultrasound device of claim 13, wherein a quantity of the power sources is 7.

17. The ultrasound device of any one of claims 1-2, wherein the multi-channel amplifier circuit further comprises a central processing unit that is configured to control the switching between the plurality of states of the multi-channel amplifier circuit.

18. The ultrasound device of any one of claims 1-2, wherein the array in which the plurality of ultrasound transducer elements are arranged comprises a linear array.

19. The ultrasound device of any one of claims 1-2, wherein the array in which the plurality of ultrasound transducer elements are arranged comprises a two dimensional array, the two dimensional array having a first array distance and direction, a second array distance and direction, and an angle between the first and second array directions.

20. The ultrasound device of claim 19, wherein the first array distance is between 50 millimeters and 150 millimeters, wherein the second array distance is between 20 millimeters and 60 millimeters, and wherein the angle between the first and second array directions is between 45 and 120 degrees.

21. The ultrasound device of claim 19, wherein the first array distance is 100 millimeters, wherein the second array distance is 30 millimeters, and wherein the angle between the first and second array directions is 90 degrees.

22. The ultrasound device of any one of claims 1-2, wherein a space between each ultrasound transducer element of the plurality of ultrasound transducer elements and the nearest neighbor comprises an air kerf of between 50 and 500 micrometers.

23. The ultrasound device of claim 22, wherein the space between each ultrasound transducer element of the plurality of ultrasound transducer elements and the nearest neighbor comprises an air kerf of about 100 micrometers.

24. The ultrasound device of claim 22, wherein the space between each ultrasound transducer element of the plurality of ultrasound transducer elements and the nearest neighbor comprises an air kerf of about 400 micrometers.

25. The ultrasound device of any one of claims 1-2, wherein the frequencies of the plurality of states of the multi-channel amplifier circuit comprise frequencies between 200 hertz and 2,000,000 hertz.

26. The ultrasound device of claim 25, wherein the frequencies of the plurality of states of the multi-channel amplifier circuit comprise a center frequency of about 500,000 hertz.

27. The ultrasound device of any one of claims 1-2, wherein the ultrasound device is configured to insonate up to 10 cm of a length of a ureter of a patient at one time.

28. The ultrasound device of any one of claims 1-2, wherein the ultrasound device is configured to insonate a ureter of a patient with a body-mass index less than or equal to 40.

29. The ultrasound device of any one of claims 1-2, wherein entry of the plurality of ultrasound transducer elements' operating variables as inputs into a computer-simulation program generates a simulated beam having a spatially uniform peak pressure distribution within a volume, and a local minimum pressure within the volume of the simulated beam that is within about 50% of a local maximum pressure within the volume of the simulated beam.

30. The ultrasound device of claim 29, wherein a local pressure within the volume of the simulated beam is between 6 MPa and 0.1 MPa.

31. The ultrasound device of any one of claims 1-2, wherein a temperature of the ultrasound transducer assembly does not surpass 43 degrees Celsius during production of the frustum-shaped beam.

32. The ultrasound device of any one of claims 1-2, wherein the ultrasound transducer assembly further comprises a standoff pad attached to a surface of the transducer assembly from which the frustum-shaped beam is produced by the plurality of ultrasound transducer elements, and wherein the standoff pad is configured to be placed in contact with skin of a patient at a location determined by using guidance from a pre-operative diagnostic tool.

33. The ultrasound device of claim 32, wherein the standoff pad is configured to be in uniform contact with skin of a patient's body.

34. The ultrasound device of claim 33, wherein the standoff pad is configured to be placed in uniform contact with the skin of the patient's body without use of real-time imaging.

35. The ultrasound device of claim 33, further comprising:
   a belt comprising a receptacle for the ultrasound transducer assembly, wherein the belt is configured to secure the ultrasound transducer assembly to be placed in uniform contact with the skin of the patient's body.

36. The ultrasound device of claim 35, wherein the belt is configured to secure the ultrasound transducer assembly at an angle relative to a plane of the skin of the patient's body.

\*    \*    \*    \*    \*